United States Patent
Johnson et al.

(10) Patent No.: US 12,364,549 B2
(45) Date of Patent: Jul. 22, 2025

(54) SELF-WINDING CABLE SURGICAL INSTRUMENTS

(71) Applicant: Cilag GmbH International, Zug (CH)

(72) Inventors: Eric N. Johnson, Maineville, OH (US); Jason Alan Hill, Loveland, OH (US)

(73) Assignee: Cilag GmbH International, Zug (CH)

( * ) Notice: Subject to any disclaimer, the term of this patent is extended or adjusted under 35 U.S.C. 154(b) by 1103 days.

(21) Appl. No.: 17/236,207

(22) Filed: Apr. 21, 2021

(65) Prior Publication Data

US 2022/0338942 A1    Oct. 27, 2022

(51) Int. Cl.
*A61B 34/30* (2016.01)
*A61B 34/00* (2016.01)
*B25J 15/00* (2006.01)
*B25J 15/04* (2006.01)

(52) U.S. Cl.
CPC .............. *A61B 34/30* (2016.02); *A61B 34/71* (2016.02); *B25J 15/0019* (2013.01); *B25J 15/0408* (2013.01); *A61B 2034/301* (2016.02); *A61B 2034/302* (2016.02); *A61B 2034/303* (2016.02); *A61B 2034/715* (2016.02)

(58) Field of Classification Search
CPC ....................................................... A61B 34/30
USPC ............................................................. 606/1
See application file for complete search history.

(56) References Cited

FOREIGN PATENT DOCUMENTS

WO    WO 2007143859 A1 * 12/2007 ............. A61B 34/77

\* cited by examiner

*Primary Examiner* — Nicole F Johnson
(74) *Attorney, Agent, or Firm* — Vorys, Sater, Seymour and Pease LLP

(57) ABSTRACT

A robotic surgical tool includes a handle having a plurality of drive inputs rotatably mounted thereto, an elongate shaft extending through the handle and having an end effector arranged at a distal end thereof, and a plurality of drive members extending along the shaft to the end effector. A plurality of input stacks are arranged within the handle and operatively coupled to the plurality of drive inputs such that actuation of the plurality of drive inputs rotates the plurality of input stacks. Each input stack includes a drive member engagement device that locates and captures a corresponding one of the plurality of drive members at the handle upon rotation of the input stack.

22 Claims, 20 Drawing Sheets

SELF-WINDING CABLE SURGICAL INSTRUMENTS

TECHNICAL FIELD

The present disclosure is related to robotic surgical systems and, more particularly, surgical instruments made of first and second matable assemblies and actuatable to engage drive members for operation.

BACKGROUND

Minimally invasive surgical (MIS) instruments are often preferred over traditional open surgical devices due to reduced post-operative recovery time and minimal scarring. Laparoscopic surgery is one type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The instruments and tools introduced into the abdominal cavity via the trocar can be used to engage and/or treat tissue in a number of ways to achieve a diagnostic or therapeutic effect.

Various robotic systems have recently been developed to assist in MIS procedures. Robotic systems can allow for more instinctive hand movements by maintaining natural eye-hand axis. Robotic systems can also allow for more degrees of freedom in movement by including an articulable "wrist" joint that creates a more natural hand-like articulation. In such systems, an end effector positioned at the distal end of the instrument can be articulated (moved) using a cable driven motion system having one or more drive cables (or other elongate members) that extend through the wrist joint. A user (e.g., a surgeon) is able to remotely operate the end effector by grasping and manipulating in space one or more controllers that communicate with a tool driver coupled to the surgical instrument. User inputs are processed by a computer system incorporated into the robotic surgical system, and the tool driver responds by actuating the cable driven motion system and thereby actively controlling the tension balance in the drive cables. Moving the drive cables articulates the end effector to desired angular positions and configurations.

Surgical instruments are complex devices with high part counts, which contributes to elevated tool costs. This can be particularly problematic for single-use disposable surgical instruments. What is needed is a surgical instrument design that mitigates the high cost of surgical instruments by including disposable and reusable parts or assemblies, which enables business objectives to be met.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview

Aspects of the present disclosure may be integrated into a robotically-enabled medical system capable of performing a variety of medical procedures, including both minimally invasive (e.g., laparoscopy) and non-invasive (e.g., endoscopy) procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance, to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto, as such concepts may have applicability throughout the entire specification.

A. Robotic System—Cart.

Figure 1:
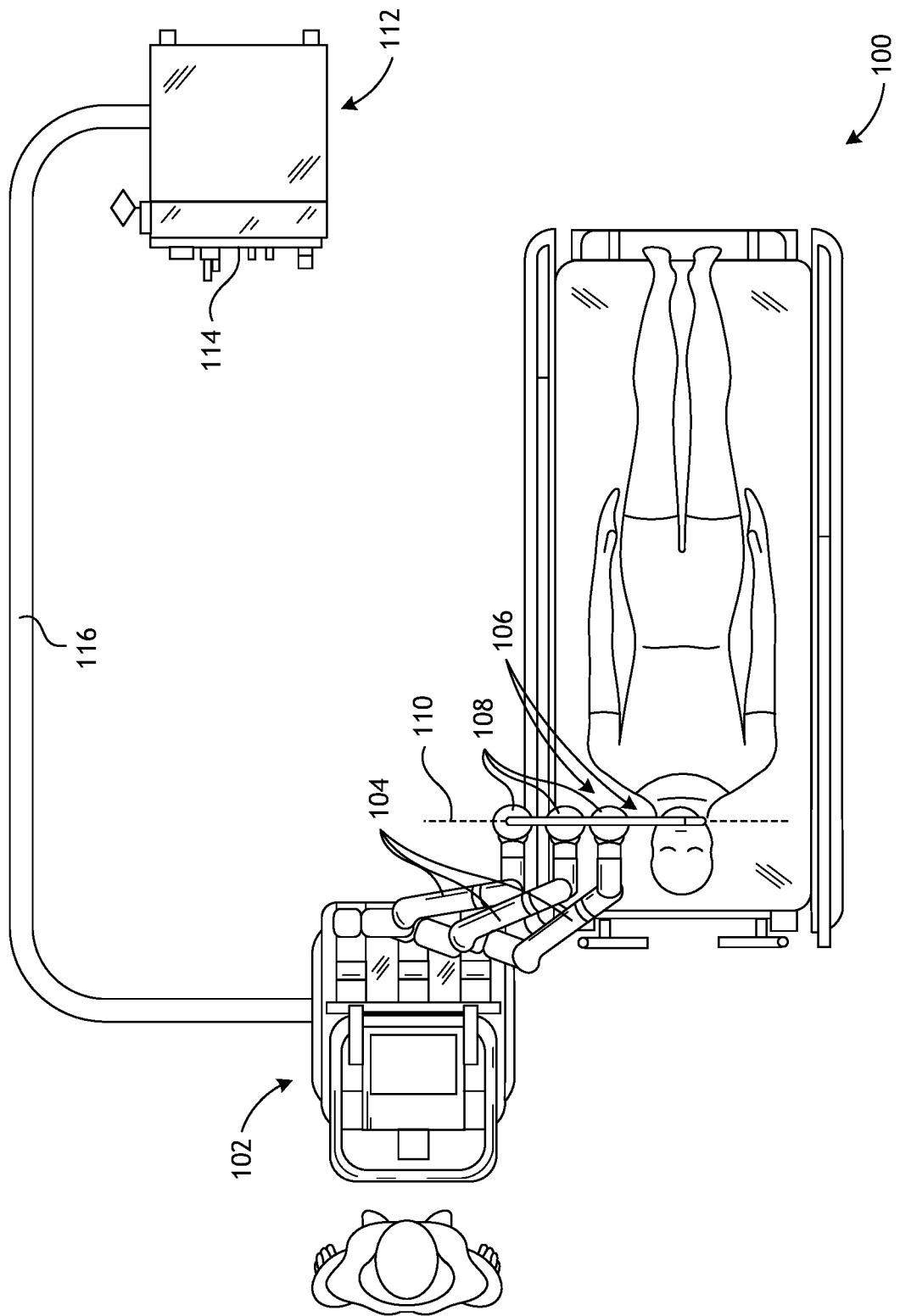
FIG. 1 illustrates an embodiment of a cart-based robotic system arranged for diagnostic and/or therapeutic bronchoscopy procedure(s).

The robotically-enabled medical system may be configured in a variety of ways depending on the particular procedure. FIG. 1 illustrates an embodiment of a cart-based robotically-enabled system 100 arranged for a diagnostic and/or therapeutic bronchoscopy procedure. For a bronchoscopy procedure, the robotic system 100 may include a cart 102 having one or more robotic arms 104 (three shown) to deliver a medical instrument (alternately referred to as a "surgical tool"), such as a steerable endoscope 106 (e.g., a procedure-specific bronchoscope for bronchoscopy), to a natural orifice access point (i.e., the mouth of the patient) to deliver diagnostic and/or therapeutic tools. As shown, the cart 102 may be positioned proximate to the patient's upper torso in order to provide access to the access point. Similarly, the robotic arms 104 may be actuated to position the bronchoscope relative to the access point. The arrangement in FIG. 1 may also be utilized when performing a gastrointestinal (GI) procedure with a gastroscope, a specialized endoscope for GI procedures.

Once the cart 102 is properly positioned adjacent the patient, the robotic arms 104 are operated to insert the steerable endoscope 106 into the patient robotically, manually, or a combination thereof. The steerable endoscope 106 may comprise at least two telescoping parts, such as an inner leader portion and an outer sheath portion, where each portion is coupled to a separate instrument driver of a set of instrument drivers 108. As illustrated, each instrument driver 108 is coupled to the distal end of a corresponding one of the robotic arms 104. This linear arrangement of the instrument drivers 108, which facilitates coaxially aligning the leader portion with the sheath portion, creates a "virtual rail" 110 that may be repositioned in space by manipulating the robotic arms 104 into different angles and/or positions. Translation of the instrument drivers 108 along the virtual rail 110 telescopes the inner leader portion relative to the outer sheath portion, thus effectively advancing or retracting the endoscope 106 relative to the patient.

As illustrated, the virtual rail 110 (and other virtual rails described herein) is depicted in the drawings using dashed lines, thus not constituting any physical structure of the system 100. The angle of the virtual rail 110 may be adjusted, translated, and pivoted based on clinical application or physician preference. For example, in bronchoscopy, the angle and position of the virtual rail 110 as shown represents a compromise between providing physician access to the endoscope 106 while minimizing friction that results from bending the endoscope 106 into the patient's mouth.

After insertion into the patient's mouth, the endoscope 106 may be directed down the patient's trachea and lungs using precise commands from the robotic system 100 until reaching a target destination or operative site. In order to enhance navigation through the patient's lung network and/or reach the desired target, the endoscope 106 may be manipulated to telescopically extend the inner leader portion from the outer sheath portion to obtain enhanced articulation and greater bend radius. The use of separate instrument drivers 108 also allows the leader portion and sheath portion to be driven independent of each other.

For example, the endoscope 106 may be directed to deliver a biopsy needle to a target, such as, for example, a lesion or nodule within the lungs of a patient. The needle may be deployed down a working channel that runs the length of the endoscope 106 to obtain a tissue sample to be analyzed by a pathologist. Depending on the pathology results, additional tools may be deployed down the working channel of the endoscope for additional biopsies. After identifying a tissue sample to be malignant, the endoscope 106 may endoscopically deliver tools to resect the potentially cancerous tissue. In some instances, diagnostic and therapeutic treatments can be delivered in separate procedures. In those circumstances, the endoscope 106 may also be used to deliver a fiducial marker to "mark" the location of a target nodule as well. In other instances, diagnostic and therapeutic treatments may be delivered during the same procedure.

The system 100 may also include a movable tower 112, which may be connected via support cables to the cart 102 to provide support for controls, electronics, fluidics, optics, sensors, and/or power to the cart 102. Placing such functionality in the tower 112 allows for a smaller form factor cart 102 that may be more easily adjusted and/or repositioned by an operating physician and his/her staff. Additionally, the division of functionality between the cart/table and the support tower 112 reduces operating room clutter and facilitates improving clinical workflow. While the cart 102 may be positioned close to the patient, the tower 112 may alternatively be stowed in a remote location to stay out of the way during a procedure.

In support of the robotic systems described above, the tower 112 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 112 or the cart 102, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, motors in the joints of the robotic arms 104 may position the arms into a certain posture or angular orientation.

The tower 112 may also include one or more of a pump, flow meter, valve control, and/or fluid access in order to provide controlled irrigation and aspiration capabilities to the system 100 that may be deployed through the endoscope 106. These components may also be controlled using the computer system of the tower 112. In some embodiments, irrigation and aspiration capabilities may be delivered directly to the endoscope 106 through separate cable(s).

The tower 112 may include a voltage and surge protector designed to provide filtered and protected electrical power to the cart 102, thereby avoiding placement of a power transformer and other auxiliary power components in the cart 102, resulting in a smaller, more moveable cart 102.

The tower 112 may also include support equipment for sensors deployed throughout the robotic system 100. For example, the tower 112 may include opto-electronics equipment for detecting, receiving, and processing data received from optical sensors or cameras throughout the robotic system 100. In combination with the control system, such opto-electronics equipment may be used to generate real-time images for display in any number of consoles deployed throughout the system, including in the tower 112. Similarly, the tower 112 may also include an electronic subsystem for receiving and processing signals received from deployed electromagnetic (EM) sensors. The tower 112 may also be used to house and position an EM field generator for detection by EM sensors in or on the medical instrument.

The tower 112 may also include a console 114 in addition to other consoles available in the rest of the system, e.g., a console mounted to the cart 102. The console 114 may include a user interface and a display screen (e.g., a touchscreen) for the physician operator. Consoles in the system 100 are generally designed to provide both robotic controls as well as pre-operative and real-time information of the procedure, such as navigational and localization information of the endoscope 106. When the console 114 is not the only console available to the physician, it may be used by a second operator, such as a nurse, to monitor the health or vitals of the patient and the operation of system, as well as provide procedure-specific data, such as navigational and localization information. In other embodiments, the console 114 may be housed in a body separate from the tower 112.

The tower 112 may be coupled to the cart 102 and endoscope 106 through one or more cables 116 connections. In some embodiments, support functionality from the tower 112 may be provided through a single cable 116 extending to the cart 102, thus simplifying and de-cluttering the operating room. In other embodiments, specific functionality may be coupled in separate cabling and connections. For example, while power may be provided through a single power cable to the cart 102, support for controls, optics, fluidics, and/or navigation may be provided through one or more separate cables.

Figure 2:
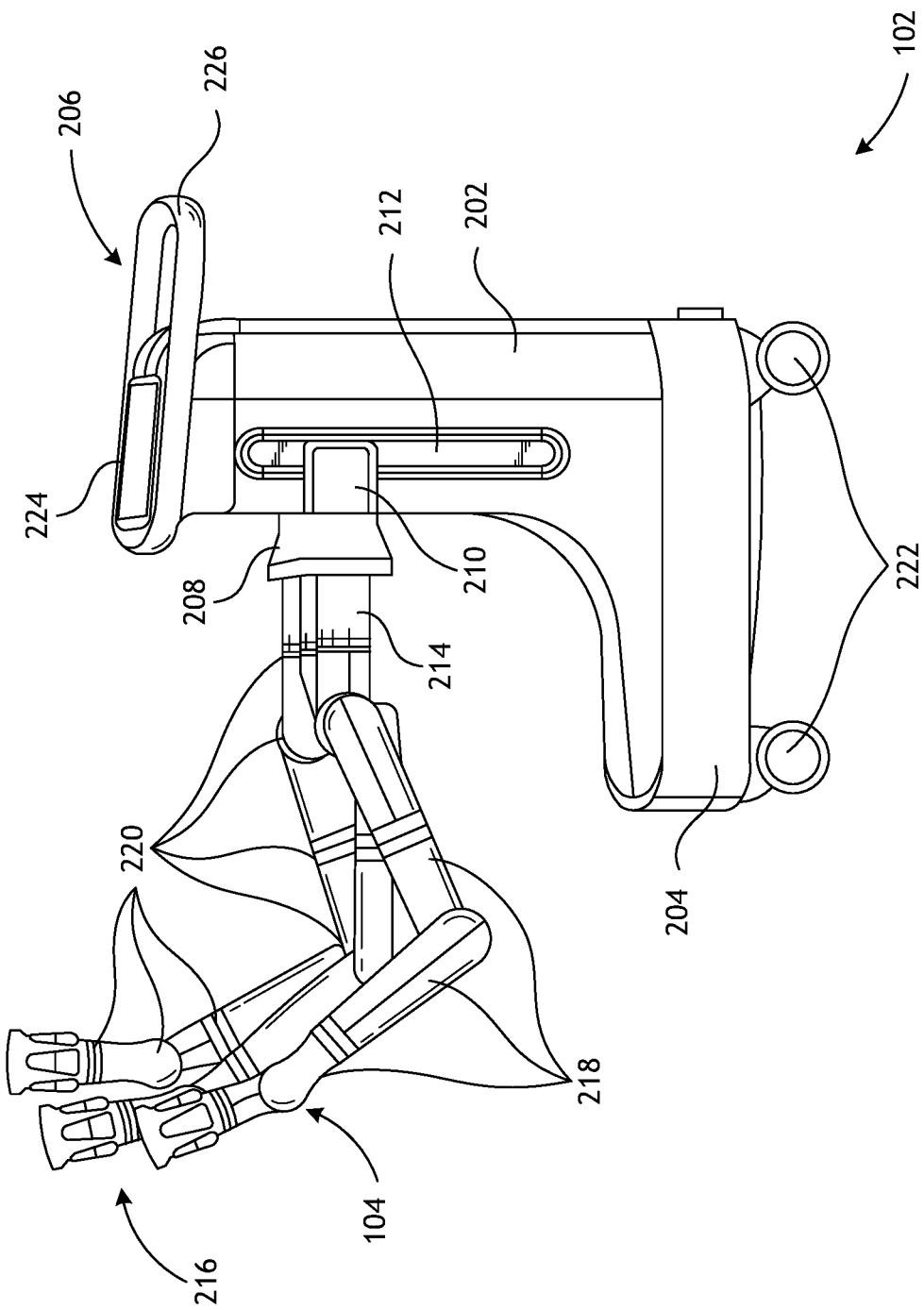
FIG. 2 depicts further aspects of the robotic system of FIG. 1.

FIG. 2 provides a detailed illustration of an embodiment of the cart 102 from the cart-based robotically-enabled system 100 of FIG. 1. The cart 102 generally includes an elongated support structure 202 (also referred to as a "column"), a cart base 204, and a console 206 at the top of the column 202. The column 202 may include one or more carriages, such as a carriage 208 (alternatively "arm support") for supporting the deployment of the robotic arms 104. The carriage 208 may include individually configurable arm mounts that rotate along a perpendicular axis to adjust the base 214 of the robotic arms 104 for better positioning relative to the patient. The carriage 208 also includes a carriage interface 210 that allows the carriage 208 to vertically translate along the column 202.

The carriage interface 210 is connected to the column 202 through slots, such as slot 212, that are positioned on opposite sides of the column 202 to guide the vertical translation of the carriage 208. The slot 212 contains a vertical translation interface to position and hold the carriage 208 at various vertical heights relative to the cart base 204. Vertical translation of the carriage 208 allows the cart 102 to adjust the reach of the robotic arms 104 to meet a variety of table heights, patient sizes, and physician preferences. Similarly, the individually configurable arm mounts on the carriage 208 allow a base 214 of the robotic arms 104 to be angled in a variety of configurations.

In some embodiments, the slot 212 may be supplemented with slot covers (not shown) that are flush and parallel to the slot surface to prevent dirt and fluid ingress into the internal chambers of the column 202 and the vertical translation interface as the carriage 208 vertically translates. The slot covers may be deployed through pairs of spring spools positioned near the vertical top and bottom of the slot 212. The covers are coiled within the spools until deployed to extend and retract from their coiled state as the carriage 208 vertically translates up and down. The spring-loading of the spools provides force to retract the cover into a spool when carriage 208 translates towards the spool, while also maintaining a tight seal when the carriage 208 translates away from the spool. The covers may be connected to the carriage 208 using, for example, brackets in the carriage interface 210 to ensure proper extension and retraction of the cover as the carriage 208 translates.

The column 202 may internally comprise mechanisms, such as gears and motors, which are designed to use a vertically aligned lead screw to translate the carriage 208 in a mechanized fashion in response to control signals generated in response to user inputs, e.g., inputs from the console 206.

The robotic arms 104 may generally comprise robotic arm bases 214 and end effectors 216 (three shown), separated by a series of linkages 218 connected by a corresponding series of joints 220, each joint 220 including an independent actuator, and each actuator including an independently controllable motor. Each independently controllable joint 220 represents an independent degree of freedom available to the corresponding robotic arm 104. In the illustrated embodiment, each arm 104 has seven joints 220, thus providing seven degrees of freedom. A multitude of joints 220 result in a multitude of degrees of freedom, allowing for "redundant" degrees of freedom. Redundant degrees of freedom allow the robotic arms 104 to position their respective end effectors 216 at a specific position, orientation, and trajectory in space using different linkage positions and joint angles. This allows for the system 100 to position and direct a medical instrument from a desired point in space while allowing the physician to move the arm joints 220 into a clinically advantageous position away from the patient to create greater access, while avoiding arm collisions.

The cart base 204 balances the weight of the column 202, the carriage 208, and the arms 104 over the floor. Accordingly, the cart base 204 houses heavier components, such as electronics, motors, power supply, as well as components that either enable movement and/or immobilize the cart. For example, the cart base 204 includes rolling casters 222 that allow for the cart to easily move around the room prior to a procedure. After reaching an appropriate position, the casters 222 may be immobilized using wheel locks to hold the cart 102 in place during the procedure.

Positioned at the vertical end of the column 202, the console 206 allows for both a user interface for receiving user input and a display screen (or a dual-purpose device such as, for example, a touchscreen 224) to provide the physician user with both pre-operative and intra-operative data. Potential pre-operative data on the touchscreen 224 may include pre-operative plans, navigation and mapping data derived from pre-operative computerized tomography (CT) scans, and/or notes from pre-operative patient interviews. Intra-operative data on the touchscreen 224 may include optical information provided from the tool, sensor and coordinate information from sensors, as well as vital patient statistics, such as respiration, heart rate, and/or pulse. The console 206 may be positioned and tilted to allow a physician to access the console from the side of the column 202 opposite carriage 208. From this position, the physician may view the console 206, the robotic arms 104, and the patient while operating the console 206 from behind the cart 102. As shown, the console 206 also includes a handle 226 to assist with maneuvering and stabilizing cart 102.

Figure 3A:
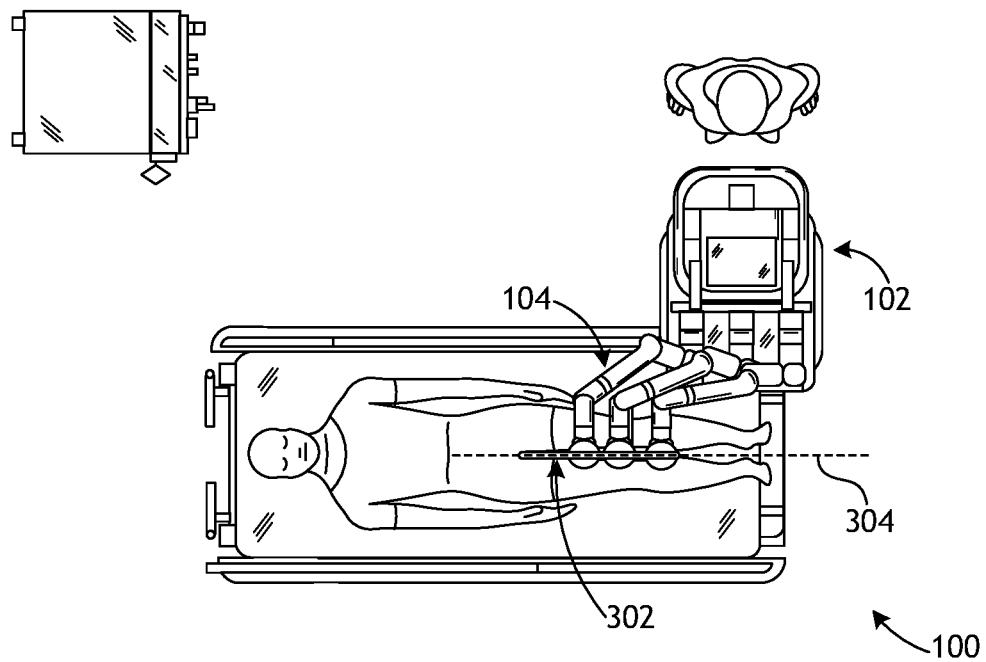
FIG. 3A illustrates an embodiment of the robotic system of FIG. 1 arranged for ureteroscopy.

FIG. 3A illustrates an embodiment of the system 100 of FIG. 1 arranged for ureteroscopy. In a ureteroscopic procedure, the cart 102 may be positioned to deliver a ureteroscope 302, a procedure-specific endoscope designed to traverse a patient's urethra and ureter, to the lower abdominal area of the patient. In ureteroscopy, it may be desirable for the ureteroscope 302 to be directly aligned with the patient's urethra to reduce friction and forces on the sensitive anatomy. As shown, the cart 102 may be aligned at the foot of the table to allow the robotic arms 104 to position the ureteroscope 302 for direct linear access to the patient's urethra. From the foot of the table, the robotic arms 104 may insert the ureteroscope 302 along a virtual rail 304 directly into the patient's lower abdomen through the urethra.

After insertion into the urethra, using similar control techniques as in bronchoscopy, the ureteroscope 302 may be navigated into the bladder, ureters, and/or kidneys for diagnostic and/or therapeutic applications. For example, the ureteroscope 302 may be directed into the ureter and kidneys to break up kidney stone build-up using a laser or ultrasonic lithotripsy device deployed down a working channel of the ureteroscope 302. After lithotripsy is complete, the resulting stone fragments may be removed using baskets deployed down the working channel of the ureteroscope 302.

Figure 3B:
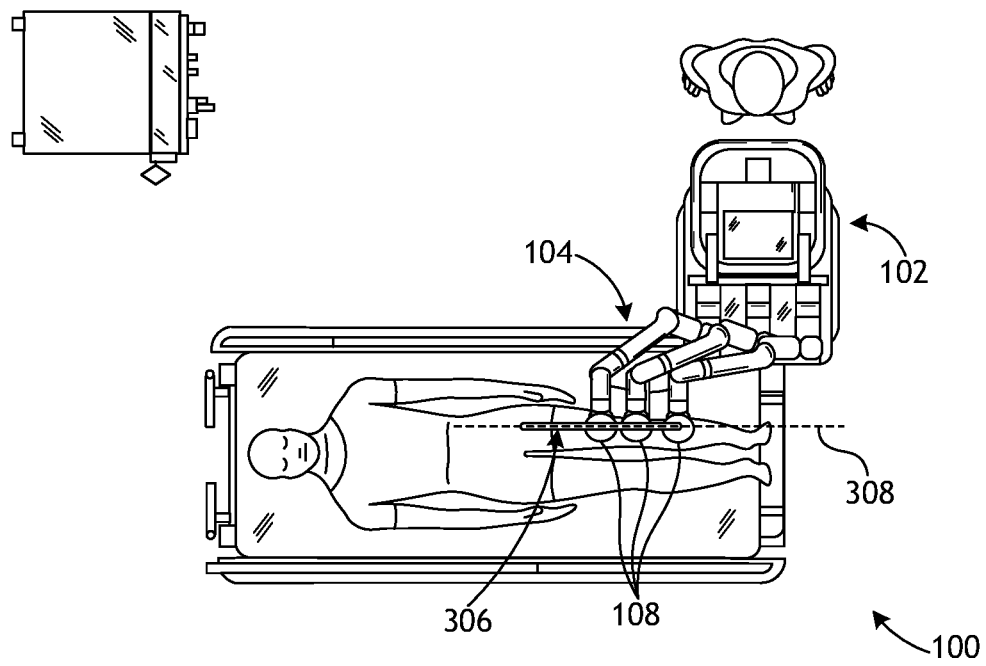
FIG. 3B illustrates an embodiment of the robotic system of FIG. 1 arranged for a vascular procedure.

FIG. 3B illustrates another embodiment of the system 100 of FIG. 1 arranged for a vascular procedure. In a vascular procedure, the system 100 may be configured such that the cart 102 may deliver a medical instrument 306, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 102 may be positioned towards the patient's legs and lower abdomen to allow the robotic arms 104 to provide a virtual rail 308 with direct linear access to the femoral artery access point in the patient's thigh/hip region. After insertion into the artery, the medical instrument 306 may be directed and advanced by translating the instrument drivers 108. Alternatively, the cart 102 may be positioned around the patient's upper abdomen in order to reach alternative vascular access points, such as, for example, the carotid and brachial arteries near the patient's shoulder and wrist.

B. Robotic System—Table.

Figure 4:
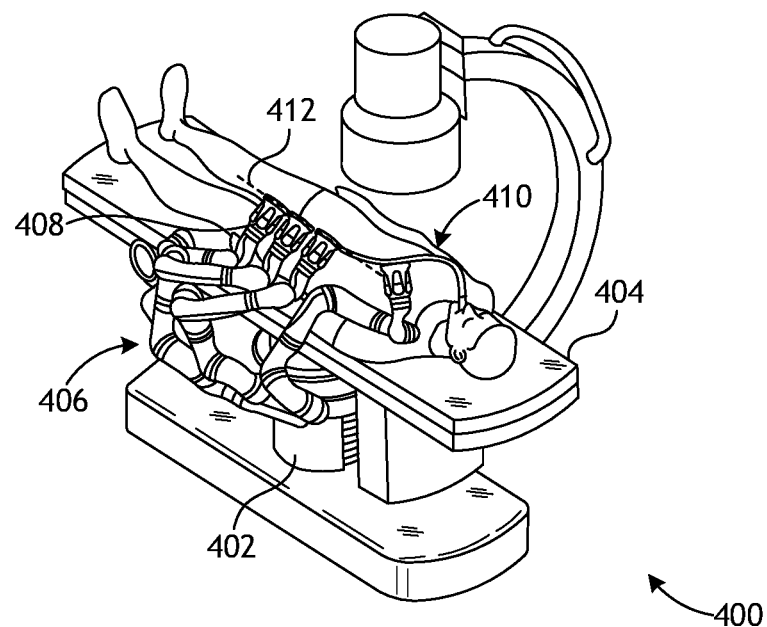
FIG. 4 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 4 illustrates an embodiment of such a robotically-enabled system 400 arranged for a bronchoscopy procedure. As illustrated, the system 400 includes a support structure or column 402 for supporting platform 404 (shown as a "table" or "bed") over the floor. Much like in the cart-based systems, the end effectors of the robotic arms 406 of the system 400 comprise instrument drivers 408 that are designed to manipulate an elongated medical instrument, such as a bronchoscope 410, through or along a virtual rail 412 formed from the linear alignment of the instrument drivers 408. In practice, a C-arm for providing fluoroscopic imaging may be positioned over the patient's upper abdominal area by placing the emitter and detector around the table 404.

Figure 5:
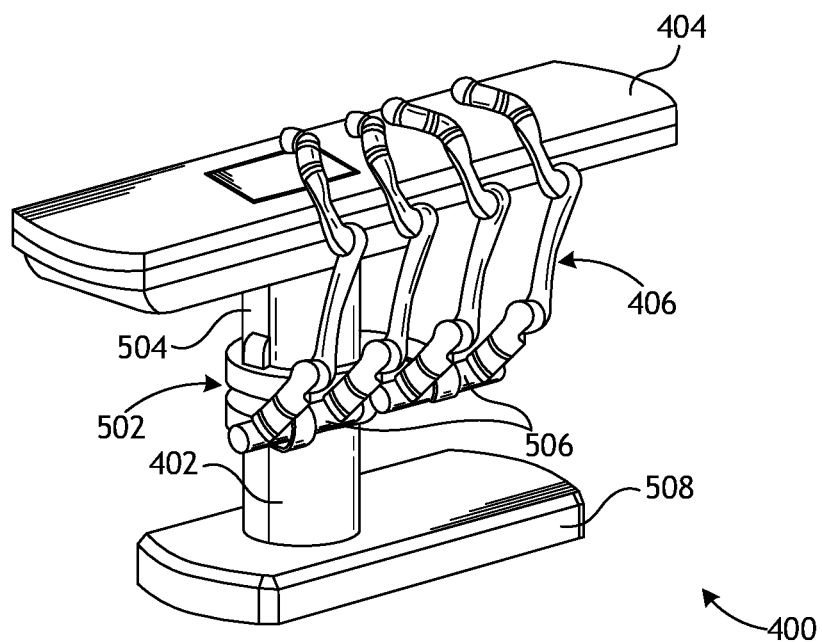
FIG. 5 provides an alternative view of the robotic system of FIG. 4.

FIG. 5 provides an alternative view of the system 400 without the patient and medical instrument for discussion purposes. As shown, the column 402 may include one or more carriages 502 shown as ring-shaped in the system 400, from which the one or more robotic arms 406 may be based. The carriages 502 may translate along a vertical column interface 504 that runs the length (height) of the column 402 to provide different vantage points from which the robotic arms 406 may be positioned to reach the patient. The carriage(s) 502 may rotate around the column 402 using a mechanical motor positioned within the column 402 to allow the robotic arms 406 to have access to multiples sides of the table 404, such as, for example, both sides of the patient. In embodiments with multiple carriages 502, the carriages 502 may be individually positioned on the column 402 and may translate and/or rotate independent of the other carriages 502. While carriages 502 need not surround the column 402 or even be circular, the ring-shape as shown facilitates rotation of the carriages 502 around the column 402 while maintaining structural balance. Rotation and translation of the carriages 502 allows the system 400 to align medical instruments, such as endoscopes and laparoscopes, into different access points on the patient.

In other embodiments (discussed in greater detail below with respect to FIG. 9A), the system 400 can include a patient table or bed with adjustable arm supports in the form of bars or rails extending alongside it. One or more robotic arms 406 (e.g., via a shoulder with an elbow joint) can be attached to the adjustable arm supports, which can be vertically adjusted. By providing vertical adjustment, the robotic arms 406 are advantageously capable of being stowed compactly beneath the patient table or bed, and subsequently raised during a procedure.

The arms 406 may be mounted on the carriages 502 through a set of arm mounts 506 comprising a series of joints that may individually rotate and/or telescopically extend to provide additional configurability to the robotic arms 406. Additionally, the arm mounts 506 may be positioned on the carriages 502 such that when the carriages 502 are appropriately rotated, the arm mounts 506 may be positioned on either the same side of the table 404 (as shown in FIG. 5), on opposite sides of table 404 (as shown in FIG. 7B), or on adjacent sides of the table 404 (not shown).

The column 402 structurally provides support for the table 404, and a path for vertical translation of the carriages 502. Internally, the column 402 may be equipped with lead screws for guiding vertical translation of the carriages, and motors to mechanize the translation of said carriages based the lead screws. The column 402 may also convey power and control signals to the carriage 502 and robotic arms 406 mounted thereon.

A table base 508 serves a similar function as the cart base 204 of the cart 102 shown in FIG. 2, housing heavier components to balance the table/bed 404, the column 402, the carriages 502, and the robotic arms 406. The table base 508 may also incorporate rigid casters to provide stability during procedures. Deployed from the bottom of the table base 508, the casters may extend in opposite directions on both sides of the base 508 and retract when the system 400 needs to be moved.

In some embodiments, the system 400 may also include a tower (not shown) that divides the functionality of system 400 between table and tower to reduce the form factor and bulk of the table 404. As in earlier disclosed embodiments, the tower may provide a variety of support functionalities to the table 404, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 508 for potential stowage of the robotic arms 406. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 6:
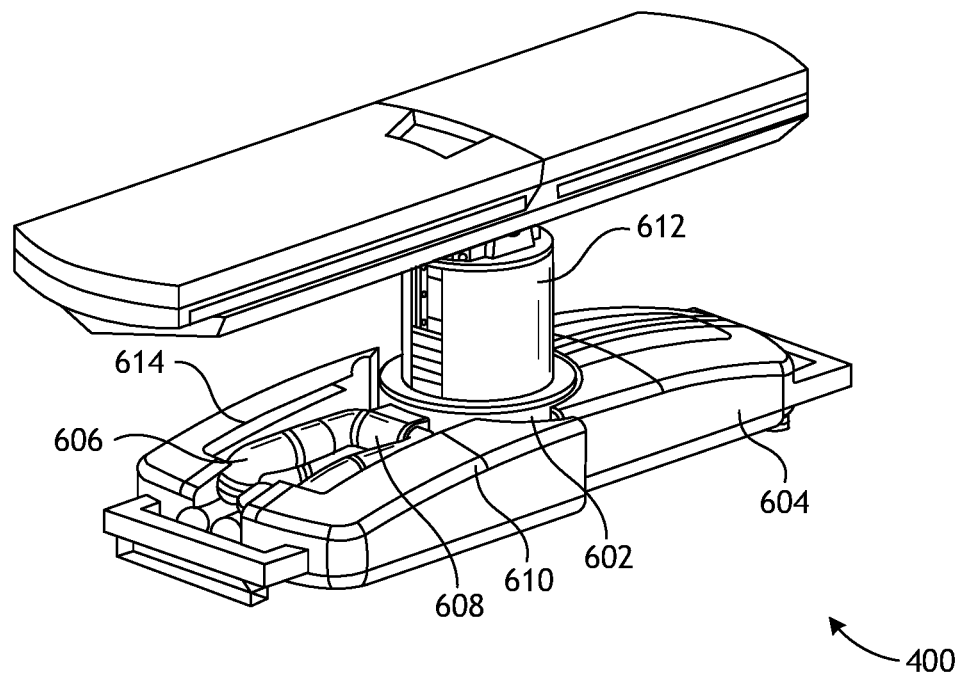
FIG. 6 illustrates an example system configured to stow robotic arm(s).

In some embodiments, a table base may stow and store the robotic arms when not in use. FIG. 6 illustrates an embodiment of the system 400 that is configured to stow robotic arms in an embodiment of the table-based system. In the system 400, one or more carriages 602 (one shown) may be vertically translated into a base 604 to stow one or more robotic arms 606, one or more arm mounts 608, and the carriages 602 within the base 604. Base covers 610 may be translated and retracted open to deploy the carriages 602, the arm mounts 608, and the arms 606 around the column 612, and closed to stow and protect them when not in use. The base covers 610 may be sealed with a membrane 614 along the edges of its opening to prevent dirt and fluid ingress when closed.

Figure 7A:
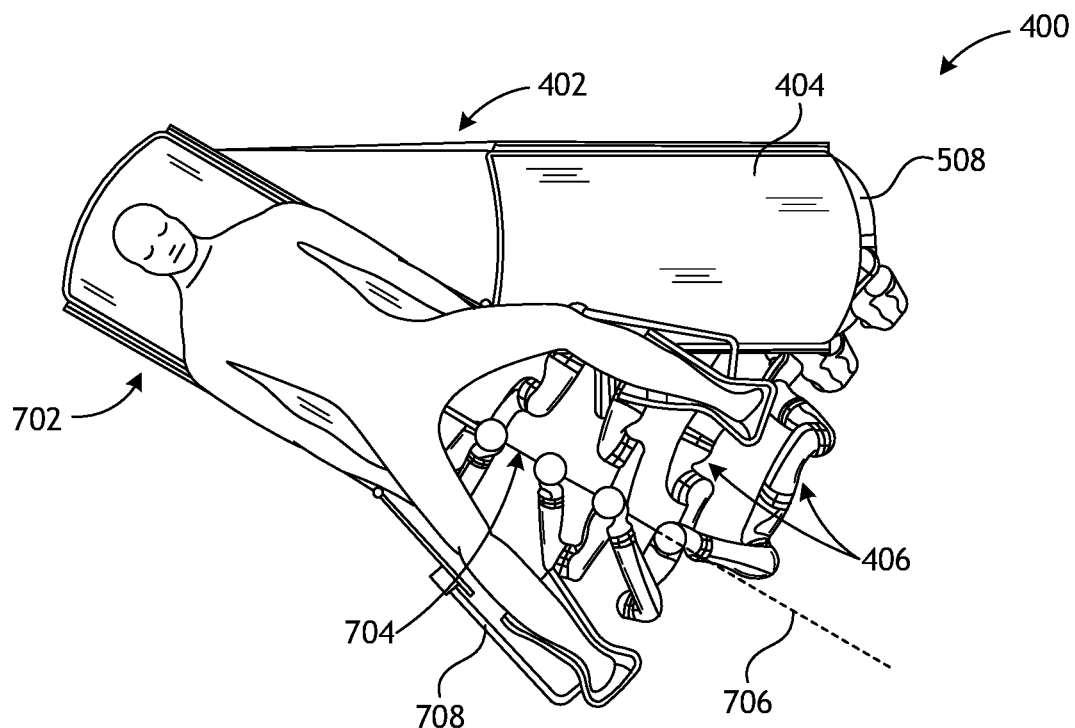
FIG. 7A illustrates an embodiment of a table-based robotic system configured for a ureteroscopy procedure.
Figure 7B:
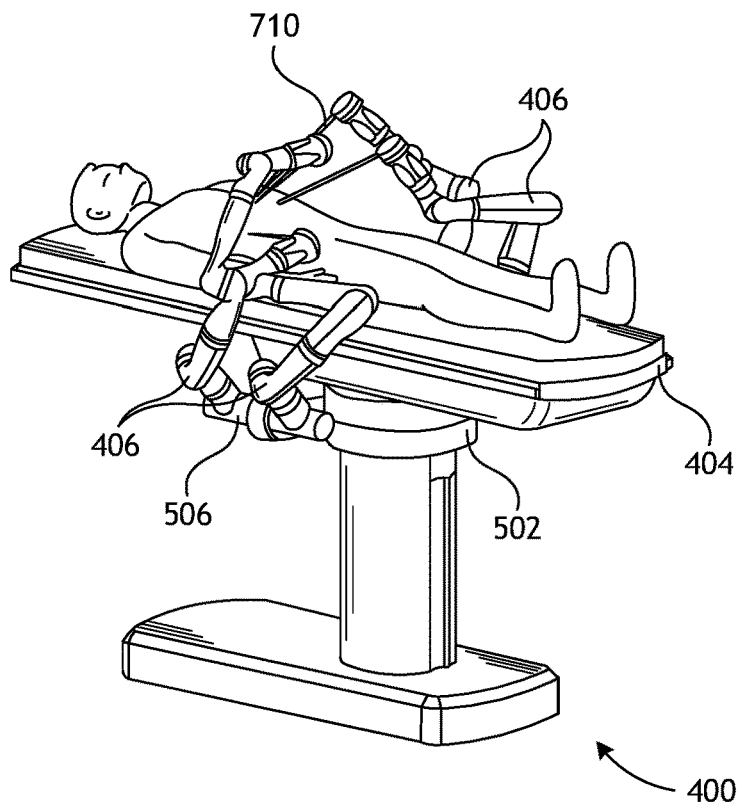
FIG. 7B illustrates an embodiment of a table-based robotic system configured for a laparoscopic procedure.

FIG. 7A illustrates an embodiment of the robotically-enabled table-based system 400 configured for a ureteroscopy procedure. In ureteroscopy, the table 404 may include a swivel portion 702 for positioning a patient off-angle from the column 402 and the table base 508. The swivel portion 702 may rotate or pivot around a pivot point (e.g., located below the patient's head) in order to position the bottom portion of the swivel portion 702 away from the column 402. For example, the pivoting of the swivel portion 702 allows a C-arm (not shown) to be positioned over the patient's lower abdomen without competing for space with the column (not shown) below table 404. By rotating the carriage (not shown) around the column 402, the robotic arms 406 may directly insert a ureteroscope 704 along a virtual rail 706 into the patient's groin area to reach the urethra. In ureteroscopy, stirrups 708 may also be fixed to the swivel portion 702 of the table 404 to support the position of the patient's legs during the procedure and allow clear access to the patient's groin area.

FIG. 7B illustrates an embodiment of the system 400 configured for a laparoscopic procedure. In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. As shown in FIG. 7B, the carriages 502 of the system 400 may be rotated and vertically adjusted to position pairs of the robotic arms 406 on opposite sides of the table 404, such that an instrument 710 may be positioned using the arm mounts 506 to be passed through minimal incisions on both sides of the patient to reach his/her abdominal cavity.

Figure 7C:
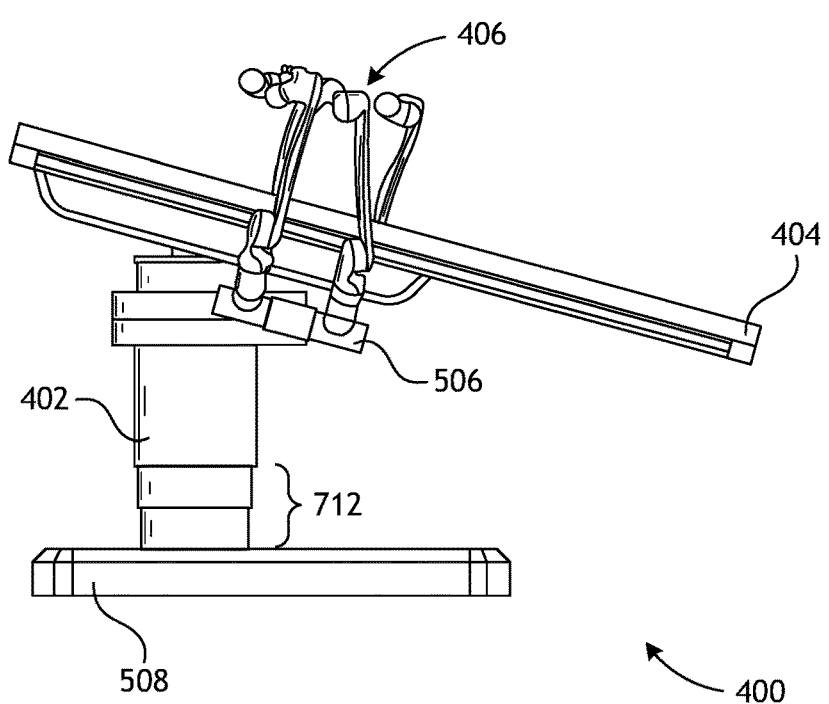
FIG. 7C illustrates an embodiment of the table-based robotic system of FIGS. 4-7B with pitch or tilt adjustment.

To accommodate laparoscopic procedures, the system 400 may also tilt the platform to a desired angle. FIG. 7C illustrates an embodiment of the system 400 with pitch or tilt adjustment. As shown in FIG. 7C, the system 400 may accommodate tilt of the table 404 to position one portion of the table 404 at a greater distance from the floor than the other. Additionally, the arm mounts 506 may rotate to match the tilt such that the arms 406 maintain the same planar relationship with table 404. To accommodate steeper angles, the column 402 may also include telescoping portions 712 that allow vertical extension of the column 402 to keep the table 404 from touching the floor or colliding with the base 508.

Figure 8:
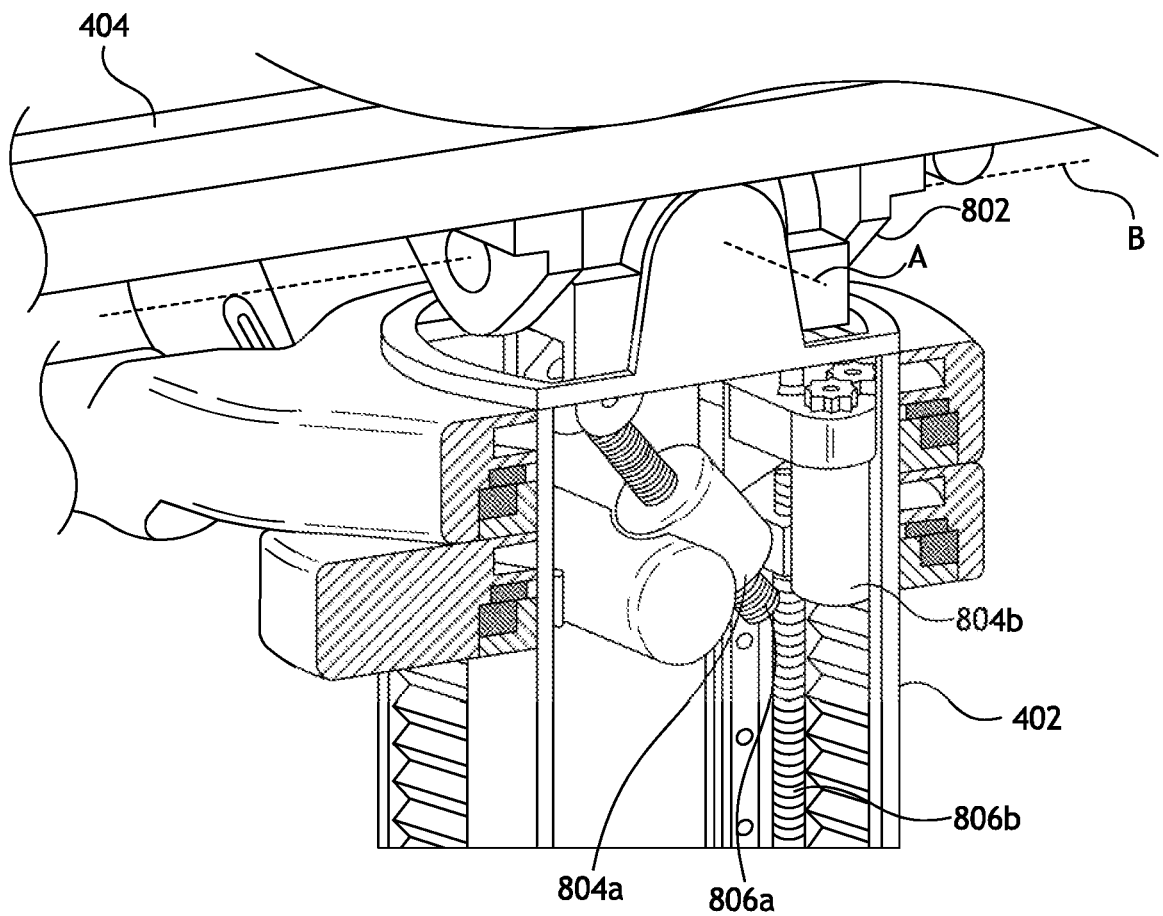
FIG. 8 provides a detailed illustration of the interface between the table and the column of the table-based robotic system of FIGS. 4-7.

FIG. 8 provides a detailed illustration of the interface between the table 404 and the column 402. Pitch rotation mechanism 802 may be configured to alter the pitch angle of the table 404 relative to the column 402 in multiple degrees of freedom. The pitch rotation mechanism 802 may be enabled by the positioning of orthogonal axes A and B at the column-table interface, each axis actuated by a separate motor 804a and 804b responsive to an electrical pitch angle command. Rotation along one screw 806a would enable tilt adjustments in one axis A, while rotation along another screw 806b would enable tilt adjustments along the other axis B. In some embodiments, a ball joint can be used to alter the pitch angle of the table 404 relative to the column 402 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 9A:
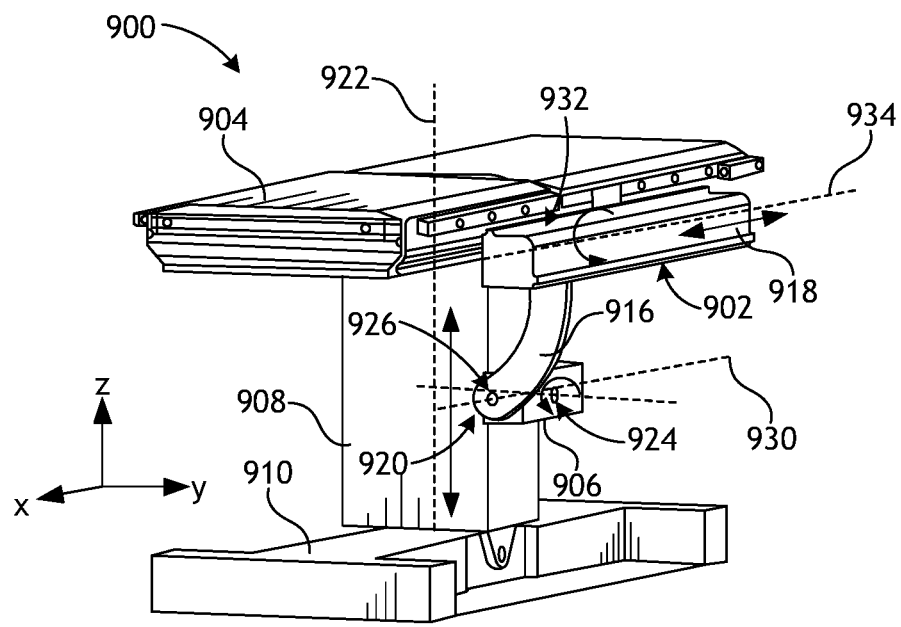
FIG. 9A illustrates an alternative embodiment of a table-based robotic system.
Figure 9B:
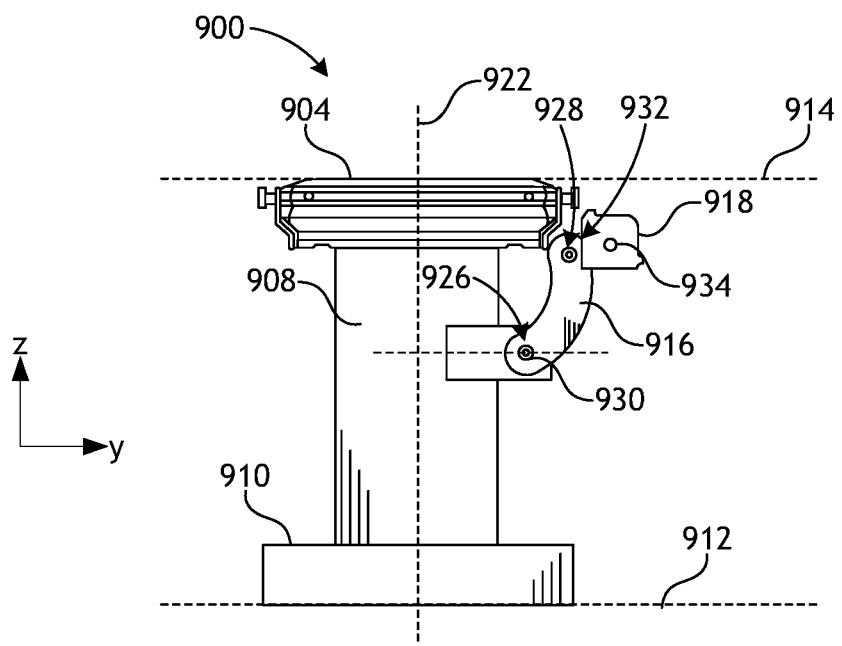
FIG. 9B illustrates an end view of the table-based robotic system of FIG. 9A.

FIGS. 9A and 9B illustrate isometric and end views, respectively, of an alternative embodiment of a table-based surgical robotics system 900. The surgical robotics system 900 includes one or more adjustable arm supports 902 that can be configured to support one or more robotic arms (see, for example, FIG. 9C) relative to a table 904. In the illustrated embodiment, a single adjustable arm support 902 is shown, though an additional arm support can be provided on an opposite side of the table 904. The adjustable arm support 902 can be configured so that it can move relative to the table 904 to adjust and/or vary the position of the adjustable arm support 902 and/or any robotic arms mounted thereto relative to the table 904. For example, the adjustable arm support 902 may be adjusted in one or more degrees of freedom relative to the table 904. The adjustable arm support 902 provides high versatility to the system 900, including the ability to easily stow the one or more adjustable arm supports 902 and any robotics arms attached thereto beneath the table 904. The adjustable arm support 902 can be elevated from the stowed position to a position below an upper surface of the table 904. In other embodiments, the adjustable arm support 902 can be elevated from the stowed position to a position above an upper surface of the table 904.

The adjustable arm support 902 can provide several degrees of freedom, including lift, lateral translation, tilt, etc. In the illustrated embodiment of FIGS. 9A and 9B, the arm support 902 is configured with four degrees of freedom, which are illustrated with arrows in FIG. 9A. A first degree of freedom allows for adjustment of the adjustable arm support 902 in the z-direction ("Z-lift"). For example, the adjustable arm support 902 can include a carriage 906 configured to move up or down along or relative to a column 908 supporting the table 904. A second degree of freedom can allow the adjustable arm support 902 to tilt. For example, the adjustable arm support 902 can include a rotary joint, which can allow the adjustable arm support 902 to be aligned with the bed in a Trendelenburg position. A third degree of freedom can allow the adjustable arm support 902 to "pivot up," which can be used to adjust a distance between a side of the table 904 and the adjustable arm support 902. A fourth degree of freedom can permit translation of the adjustable arm support 902 along a longitudinal length of the table.

The surgical robotics system 900 in FIGS. 9A and 9B can comprise a table 904 supported by a column 908 that is mounted to a base 910. The base 910 and the column 908 support the table 904 relative to a support surface. A floor axis 912 and a support axis 914 are shown in FIG. 9B.

The adjustable arm support 902 can be mounted to the column 908. In other embodiments, the arm support 902 can be mounted to the table 904 or the base 910. The adjustable arm support 902 can include a carriage 906, a bar or rail connector 916 and a bar or rail 918. In some embodiments, one or more robotic arms mounted to the rail 918 can translate and move relative to one another.

The carriage 906 can be attached to the column 908 by a first joint 920, which allows the carriage 906 to move relative to the column 908 (e.g., such as up and down a first or vertical axis 922). The first joint 920 can provide the first degree of freedom ("Z-lift") to the adjustable arm support 902. The adjustable arm support 902 can include a second joint 924, which provides the second degree of freedom (tilt) for the adjustable arm support 902. The adjustable arm support 902 can include a third joint 926, which can provide the third degree of freedom ("pivot up") for the adjustable arm support 902. An additional joint 928 (shown in FIG. 9B) can be provided that mechanically constrains the third joint 926 to maintain an orientation of the rail 918 as the rail connector 916 is rotated about a third axis 930. The adjustable arm support 902 can include a fourth joint 932, which can provide a fourth degree of freedom (translation) for the adjustable arm support 902 along a fourth axis 934.

Figure 9C:
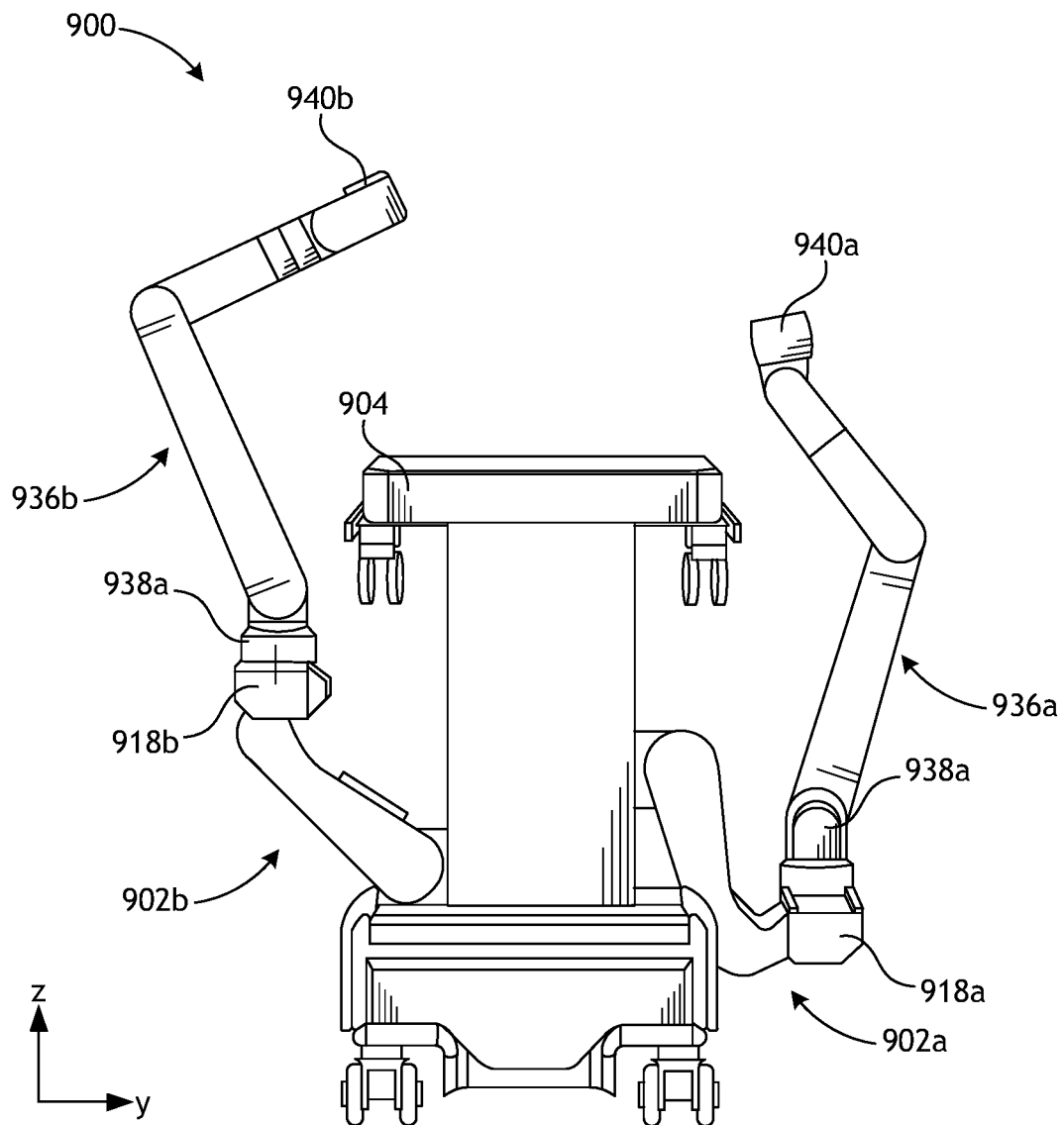
FIG. 9C illustrates an end view of a table-based robotic system with robotic arms attached thereto.

FIG. 9C illustrates an end view of the surgical robotics system 900 with two adjustable arm supports 902a and 902b mounted on opposite sides of the table 904. A first robotic arm 936a is attached to the first bar or rail 918a of the first adjustable arm support 902a. The first robotic arm 936a includes a base 938a attached to the first rail 918a. The distal end of the first robotic arm 936a includes an instrument drive mechanism or input 940a that can attach to one or more robotic medical instruments or tools. Similarly, the second robotic arm 936b includes a base 938a attached to the second rail 918b. The distal end of the second robotic arm 936b includes an instrument drive mechanism or input 940b configured to attach to one or more robotic medical instruments or tools.

In some embodiments, one or more of the robotic arms 936a,b comprises an arm with seven or more degrees of freedom. In some embodiments, one or more of the robotic arms 936a,b can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 938a,b (1-degree of freedom including translation). In some embodiments, the insertion degree of freedom can be provided by the robotic arm 936a,b, while in other embodiments, the instrument itself provides insertion via an instrument-based insertion architecture.

C. Instrument Driver & Interface.

The end effectors of a system's robotic arms comprise (i) an instrument driver (alternatively referred to as "tool driver," "instrument drive mechanism," "instrument device manipulator," and "drive input") that incorporate electro-mechanical means for actuating the medical instrument, and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 10:
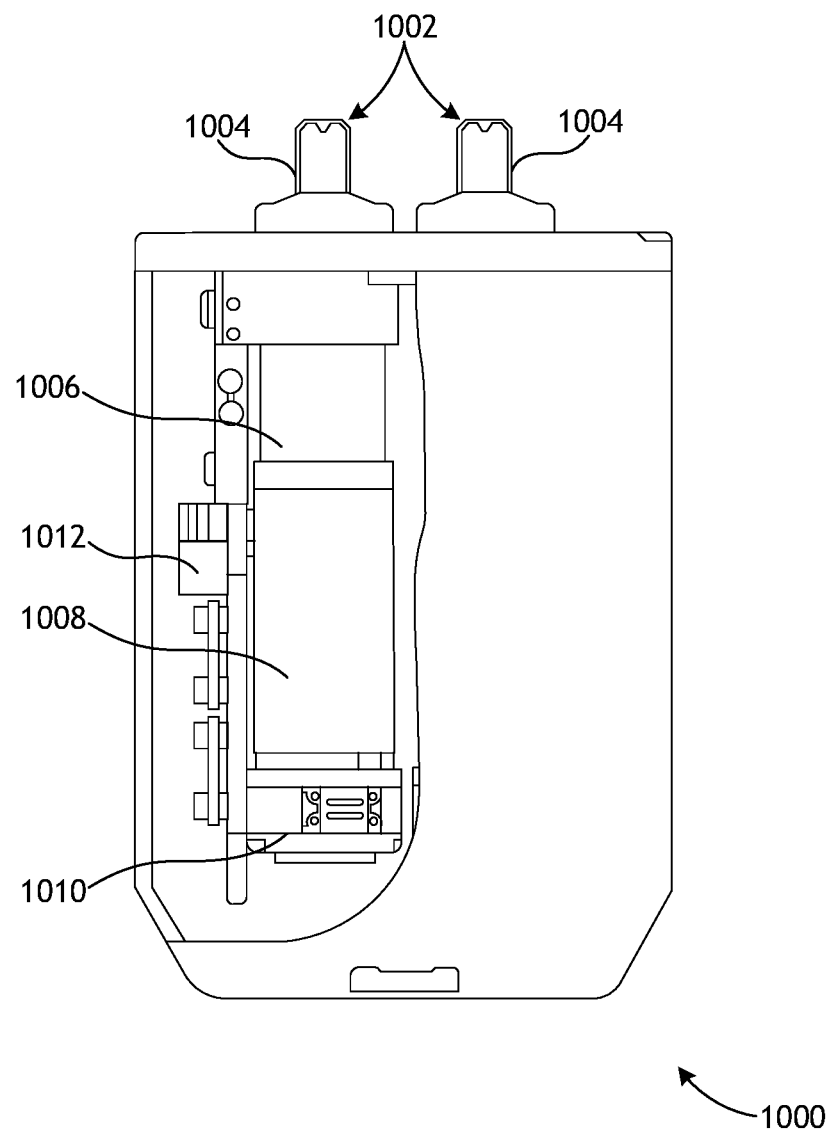
FIG. 10 illustrates an exemplary instrument driver.

FIG. 10 illustrates an example instrument driver 1000, according to one or more embodiments. Positioned at the distal end of a robotic arm, the instrument driver 1000 includes one or more drive outputs 1002 arranged with parallel axes to provide controlled torque to a medical instrument via corresponding drive shafts 1004. Each drive output 1002 comprises an individual drive shaft 1004 for interacting with the instrument, a gear head 1006 for converting the motor shaft rotation to a desired torque, a motor 1008 for generating the drive torque, and an encoder 1010 to measure the speed of the motor shaft and provide feedback to control circuitry 1012, which can also be used for receiving control signals and actuating the drive output 1002. Each drive output 1002 being independently controlled and motorized, the instrument driver 1000 may provide multiple (at least two shown in FIG. 10) independent drive outputs to the medical instrument. In operation, the control circuitry 1012 receives a control signal, transmits a motor signal to the motor 1008, compares the resulting motor speed as measured by the encoder 1010 with the desired speed, and modulates the motor signal to generate the desired torque.

For procedures that require a sterile environment, the robotic system may incorporate a drive interface, such as a sterile adapter connected to a sterile drape that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 11:
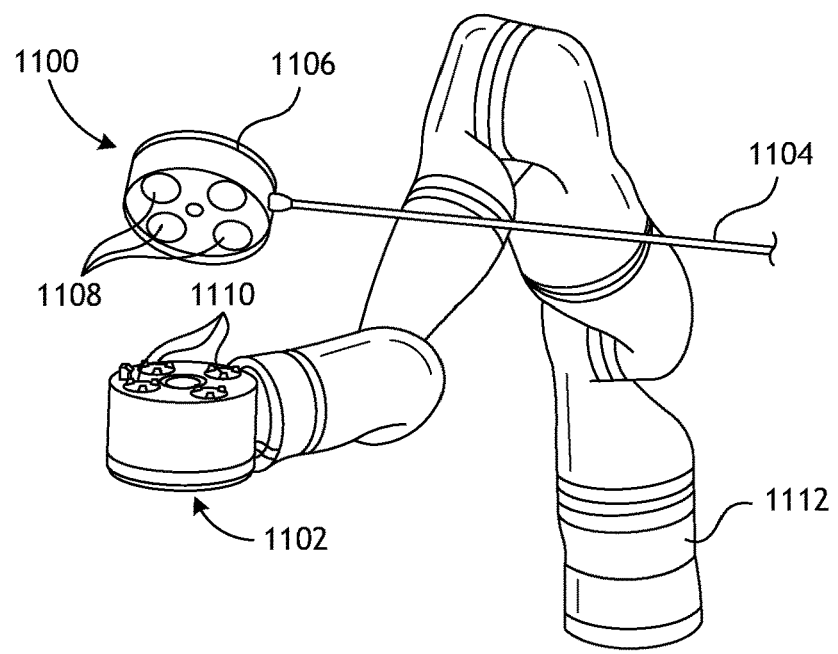
FIG. 11 illustrates an exemplary medical instrument with a paired instrument driver.

FIG. 11 illustrates an example medical instrument 1100 with a paired instrument driver 1102. Like other instruments designed for use with a robotic system, the medical instrument 1100 (alternately referred to as a "surgical tool") comprises an elongated shaft 1104 (or elongate body) and an instrument base 1106. The instrument base 1106, also referred to as an "instrument handle" due to its intended design for manual interaction by the physician, may generally comprise rotatable drive inputs 1108, e.g., receptacles, pulleys or spools, that are designed to be mated with drive outputs 1110 that extend through a drive interface on the instrument driver 1102 at the distal end of a robotic arm 1112. When physically connected, latched, and/or coupled, the mated drive inputs 1108 of the instrument base 1106 may share axes of rotation with the drive outputs 1110 in the instrument driver 1102 to allow the transfer of torque from the drive outputs 1110 to the drive inputs 1108. In some embodiments, the drive outputs 1110 may comprise splines that are designed to mate with receptacles on the drive inputs 1108.

The elongated shaft 1104 is designed to be delivered through either an anatomical opening or lumen, e.g., as in endoscopy, or a minimally invasive incision, e.g., as in laparoscopy. The elongated shaft 1104 may be either flexible (e.g., having properties similar to an endoscope) or rigid (e.g., having properties similar to a laparoscope) or contain a customized combination of both flexible and rigid portions. When designed for laparoscopy, the distal end of the shaft 1104 may be connected to an end effector extending from a jointed wrist formed from a clevis with at least one degree of freedom and a surgical tool or medical instrument, such as, for example, a grasper or scissors, that may be actuated based on force from the tendons as the drive inputs 1008 rotate in response to torque received from the drive outputs 1110 of the instrument driver 1102. When designed for endoscopy, the distal end of the flexible elongated shaft 1104 may include a steerable or controllable bending section that may be articulated and bent based on torque received from the drive outputs 1110 of the instrument driver 1102.

In some embodiments, torque from the instrument driver 1102 is transmitted down the elongated shaft 1104 using tendons along the shaft 1104. These individual tendons, such as pull wires, may be individually anchored to individual drive inputs 1108 within the instrument handle 1106. From the handle 1106, the tendons are directed down one or more pull lumens along the elongated shaft 1104 and anchored at the distal portion of the elongated shaft 1104, or in the wrist at the distal portion of the elongated shaft. During a surgical procedure, such as a laparoscopic, endoscopic, or a hybrid procedure, these tendons may be coupled to a distally mounted end effector, such as a wrist, a grasper, or scissors. Under such an arrangement, torque exerted on the drive inputs 1108 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 1104, where tension from the tendon cause the grasper to close.

In endoscopy, the tendons may be coupled to a bending or articulating section positioned along the elongated shaft 1104 (e.g., at the distal end) via adhesive, control ring, or other mechanical fixation. When fixedly attached to the distal end of a bending section, torque exerted on drive inputs 1108 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 1104 to allow for controlled articulation in the desired bending or articulable sections.

In endoscopy, the elongated shaft 1104 houses a number of components to assist with the robotic procedure. The shaft may comprise a working channel for deploying surgical tools (or medical instruments), irrigation, and/or aspiration to the operative region at the distal end of the shaft 1104. The shaft 1104 may also accommodate wires and/or optical fibers to transfer signals to/from an optical assembly at the distal tip, which may include of an optical camera. The shaft 1104 may also accommodate optical fibers to carry light from proximally-located light sources, such as light emitting diodes, to the distal end of the shaft.

At the distal end of the instrument 1100, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 11, the drive shaft axes, and thus the drive input axes, are orthogonal to the axis of the elongated shaft. This arrangement, however, complicates roll capabilities for the elongated shaft 1104. Rolling the elongated shaft 1104 along its axis while keeping the drive inputs 1108 static results in undesirable tangling of the tendons as they extend off the drive inputs 1108 and enter pull lumens within the elongated shaft 1104. The resulting entanglement of such tendons may disrupt any control algorithms intended to predict movement of the flexible elongated shaft during an endoscopic procedure.

Figure 12:
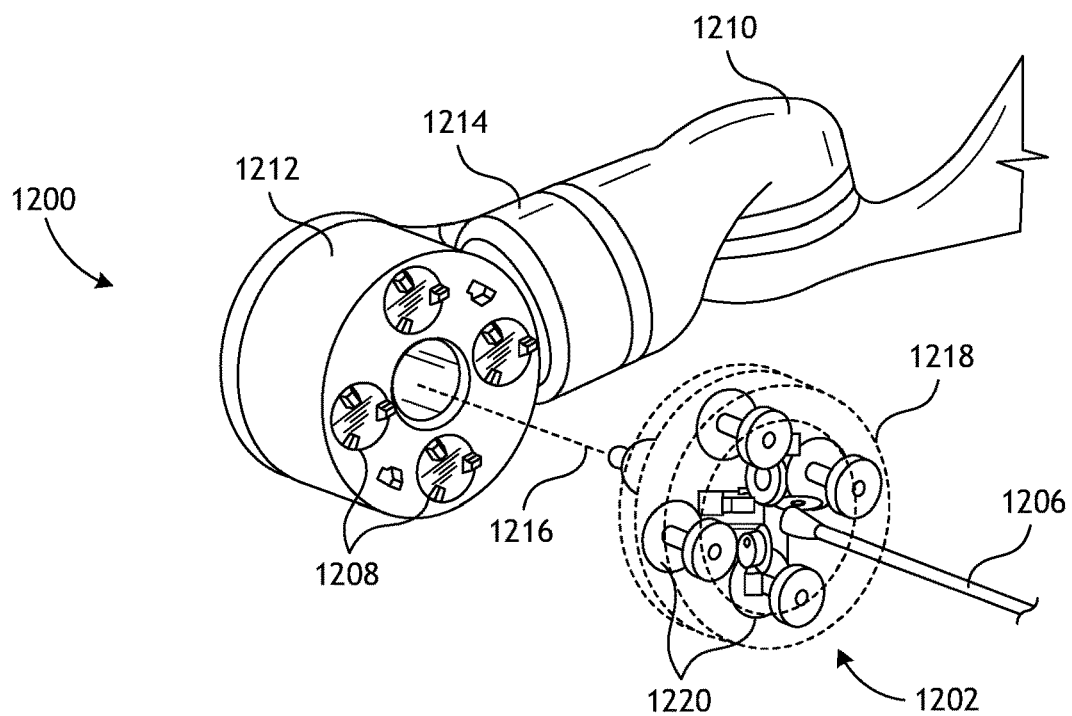
FIG. 12 illustrates an alternative design for an instrument driver and instrument where the axes of the drive units are parallel to the axis of the elongated shaft of the instrument.

FIG. 12 illustrates an alternative design for a circular instrument driver 1200 and corresponding instrument 1202 (alternately referred to as a "surgical tool") where the axes of the drive units are parallel to the axis of the elongated shaft 1206 of the instrument 1202. As shown, the instrument driver 1200 comprises four drive units with corresponding drive outputs 1208 aligned in parallel at the end of a robotic arm 1210. The drive units and their respective drive outputs 1208 are housed in a rotational assembly 1212 of the instrument driver 1200 that is driven by one of the drive units within the assembly 1212. In response to torque provided by the rotational drive unit, the rotational assembly 1212 rotates along a circular bearing that connects the rotational assembly 1212 to a non-rotational portion 1214 of the instrument driver 1200. Power and control signals may be communicated from the non-rotational portion 1214 of the instrument driver 1200 to the rotational assembly 1212 through electrical contacts maintained through rotation by a brushed slip ring connection (not shown). In other embodiments, the rotational assembly 1212 may be responsive to a separate drive unit that is integrated into the non-rotatable portion 1214, and thus not in parallel with the other drive units. The rotational assembly 1212 allows the instrument driver 1200 to rotate the drive units and their respective drive outputs 1208 as a single unit around an instrument driver axis 1216.

Like earlier disclosed embodiments, the instrument 1202 may include an elongated shaft 1206 and an instrument base 1218 (shown in phantom) including a plurality of drive inputs 1220 (such as receptacles, pulleys, and spools) that are configured to mate with the drive outputs 1208 of the instrument driver 1200. Unlike prior disclosed embodiments, the instrument shaft 1206 extends from the center of the instrument base 1218 with an axis substantially parallel to the axes of the drive inputs 1220, rather than orthogonal as in the design of FIG. 11.

When coupled to the rotational assembly 1212 of the instrument driver 1200, the medical instrument 1202, comprising instrument base 1218 and instrument shaft 1206, rotates in combination with the rotational assembly 1212 about the instrument driver axis 1216. Since the instrument shaft 1206 is positioned at the center of the instrument base 1218, the instrument shaft 1206 is coaxial with the instrument driver axis 1216 when attached. Thus, rotation of the rotational assembly 1212 causes the instrument shaft 1206 to rotate about its own longitudinal axis. Moreover, as the instrument base 1218 rotates with the instrument shaft 1206, any tendons connected to the drive inputs 1220 in the instrument base 1218 are not tangled during rotation. Accordingly, the parallelism of the axes of the drive outputs 1208, the drive inputs 1220, and the instrument shaft 1206 allows for the shaft rotation without tangling any control tendons.

Figure 13:
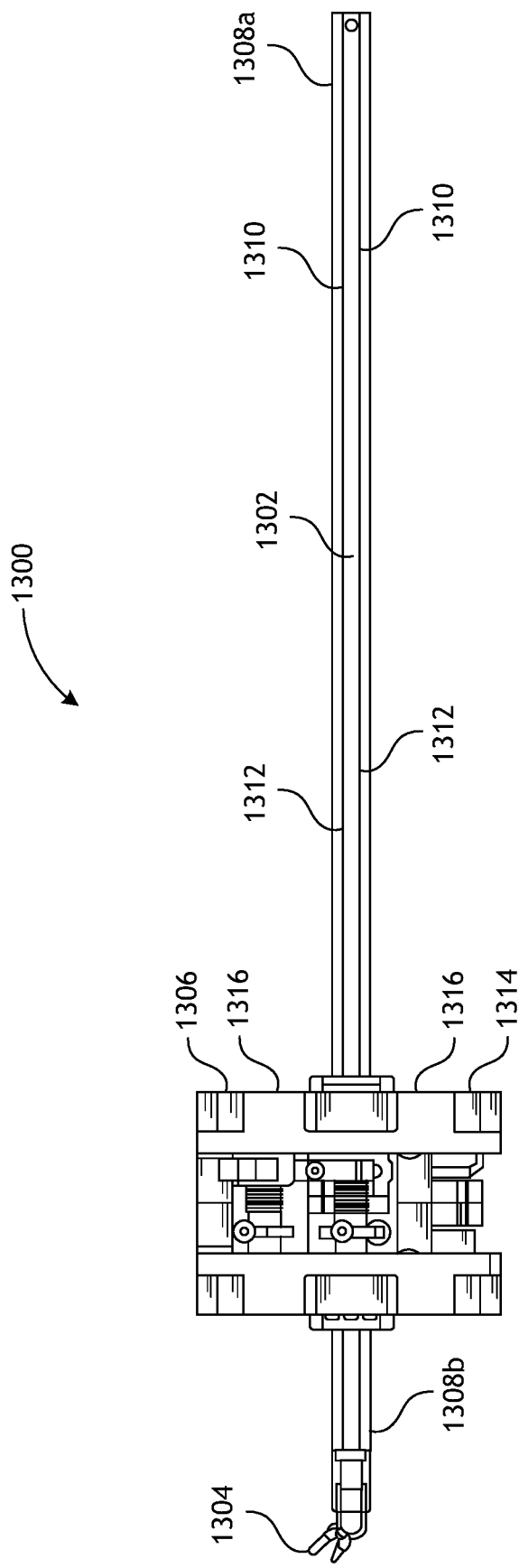
FIG. 13 illustrates an instrument having an instrument-based insertion architecture.

FIG. 13 illustrates a medical instrument 1300 having an instrument based insertion architecture in accordance with some embodiments. The instrument 1300 (alternately referred to as a "surgical tool") can be coupled to any of the instrument drivers discussed herein above and, as illustrated, can include an elongated shaft 1302, an end effector 1304 connected to the shaft 1302, and a handle 1306 coupled to the shaft 1302. The elongated shaft 1302 comprises a tubular member having a proximal portion 1308a and a distal portion 1308b. The elongated shaft 1302 comprises one or more channels or grooves 1310 along its outer surface and configured to receive one or more wires or cables 1312 therethrough. One or more cables 1312 thus run along an outer surface of the elongated shaft 1302. In other embodiments, the cables 1312 can also run through the elongated shaft 1302. Manipulation of the cables 1312 (e.g., via an instrument driver) results in actuation of the end effector 1304.

The instrument handle 1306, which may also be referred to as an instrument base, may generally comprise an attachment interface 1314 having one or more mechanical inputs 1316, e.g., receptacles, pulleys or spools, that are designed to be reciprocally mated with one or more drive outputs on an attachment surface of an instrument driver.

In some embodiments, the instrument 1300 comprises a series of pulleys or cables that enable the elongated shaft 1302 to translate relative to the handle 1306. In other words, the instrument 1300 itself comprises an instrument-based insertion architecture that accommodates insertion of the instrument 1300, thereby minimizing the reliance on a robot arm to provide insertion of the instrument 1300. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 14:
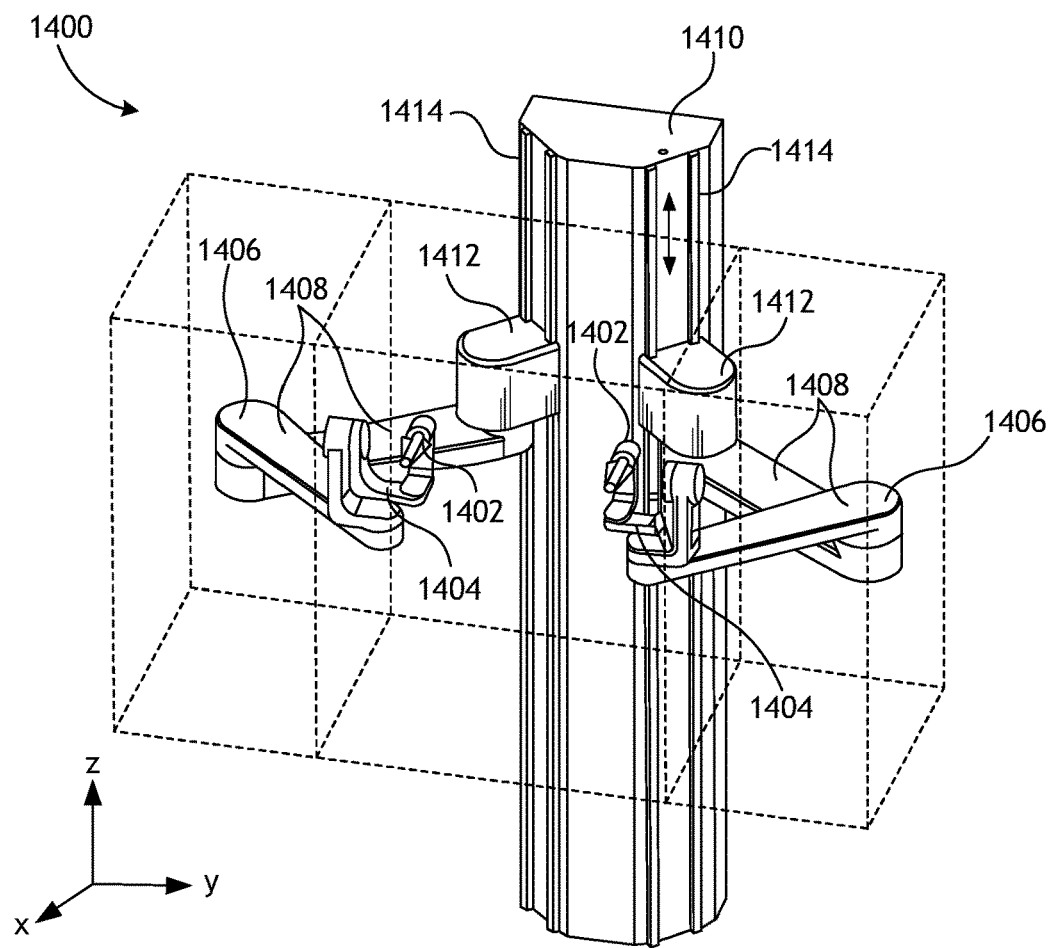
FIG. 14 illustrates an exemplary controller.

FIG. 14 is a perspective view of an embodiment of a controller 1400. In the present embodiment, the controller 1400 comprises a hybrid controller that can have both impedance and admittance control. In other embodiments, the controller 1400 can utilize just impedance or passive control. In other embodiments, the controller 1400 can utilize just admittance control. By being a hybrid controller, the controller 1400 advantageously can have a lower perceived inertia while in use.

In the illustrated embodiment, the controller 1400 is configured to allow manipulation of two medical instruments, and includes two handles 1402. Each of the handles 1402 is connected to a gimbal 1404, and each gimbal 1404 is connected to a positioning platform 1406.

As shown in FIG. 14, each positioning platform 1406 includes a selective compliance assembly robot arm (SCARA) 1408 coupled to a column 1410 by a prismatic joint 1412. The prismatic joints 1412 are configured to translate along the column 1410 (e.g., along rails 1414) to allow each of the handles 1402 to be translated in the z-direction, providing a first degree of freedom. The SCARA arm 1408 is configured to allow motion of the handle 1402 in an x-y plane, providing two additional degrees of freedom.

In some embodiments, one or more load cells are positioned in the controller 1400. For example, in some embodiments, a load cell (not shown) is positioned in the body of each of the gimbals 1404. By providing a load cell, portions of the controller 1400 are capable of operating under admittance control, thereby advantageously reducing the perceived inertia of the controller 1400 while in use. In some embodiments, the positioning platform 1406 is configured for admittance control, while the gimbal 1404 is configured for impedance control. In other embodiments, the gimbal 1404 is configured for admittance control, while the positioning platform 1406 is configured for impedance control. Accordingly, for some embodiments, the translational or positional degrees of freedom of the positioning platform 1406 can rely on admittance control, while the rotational degrees of freedom of the gimbal 1404 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
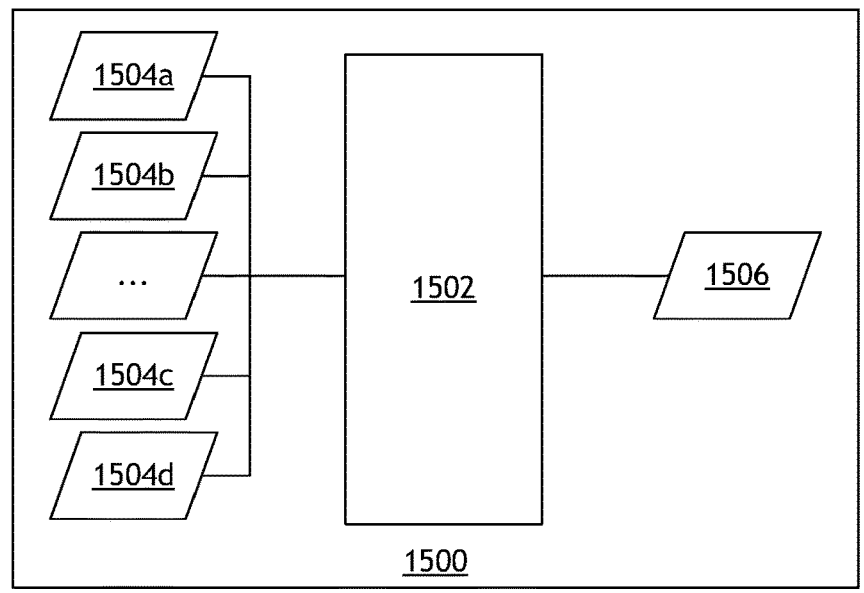
FIG. 15 depicts a block diagram illustrating a localization system that estimates a location of one or more elements of the robotic systems of FIGS. 1-7C, such as the location of the instrument of FIGS. 11-13, in accordance to an example embodiment.

FIG. 15 is a block diagram illustrating a localization system 1500 that estimates a location of one or more elements of the robotic system, such as the location of the instrument, in accordance to an example embodiment. The localization system 1500 may be a set of one or more computer devices configured to execute one or more instructions. The computer devices may be embodied by a processor (or processors) and computer-readable memory in one or more components discussed above. By way of example and not limitation, the computer devices may be in the tower 112 shown in FIG. 1, the cart 102 shown in FIGS. 1-3B, the beds shown in FIGS. 4-9, etc.

As shown in FIG. 15, the localization system 1500 may include a localization module 1502 that processes input data 1504a, 1504b, 1504c, and 1504d to generate location data 1506 for the distal tip of a medical instrument. The location data 1506 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 1504a-d are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 1504a (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 1504b. The localization module 1502 may process the vision data 1504b to enable one or more vision-based location tracking. For example, the preoperative model data may be used in conjunction with the vision data 1504b to enable computer vision-based tracking of the medical instrument (e.g., an endoscope or an instrument advance through a working channel of the endoscope). For example, using the preoperative model data 1504a, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 1502 may identify circular geometries in the preoperative model data 1504a that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 1504b to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 1502 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 1504c. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 1504d may also be used by the localization module 1502 to provide localization data 1506 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 1502. For example, although not shown in FIG. 15, an instrument utilizing shape-sensing fiber can provide shape data that the localization module 1502 can use to determine the location and shape of the instrument.

The localization module 1502 may use the input data 1504a-d in combination(s). In some cases, such a combination may use a probabilistic approach where the localization module 1502 assigns a confidence weight to the location determined from each of the input data 1504a-d. Thus, where the EM data 1504c may not be reliable (as may be the case where there is EM interference) the confidence of the location determined by the EM data 1504c can be decrease and the localization module 1502 may rely more heavily on the vision data 1504*b* and/or the robotic command and kinematics data 1504*d*.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Description

Self-Winding Cable Instrument

Figure 16:
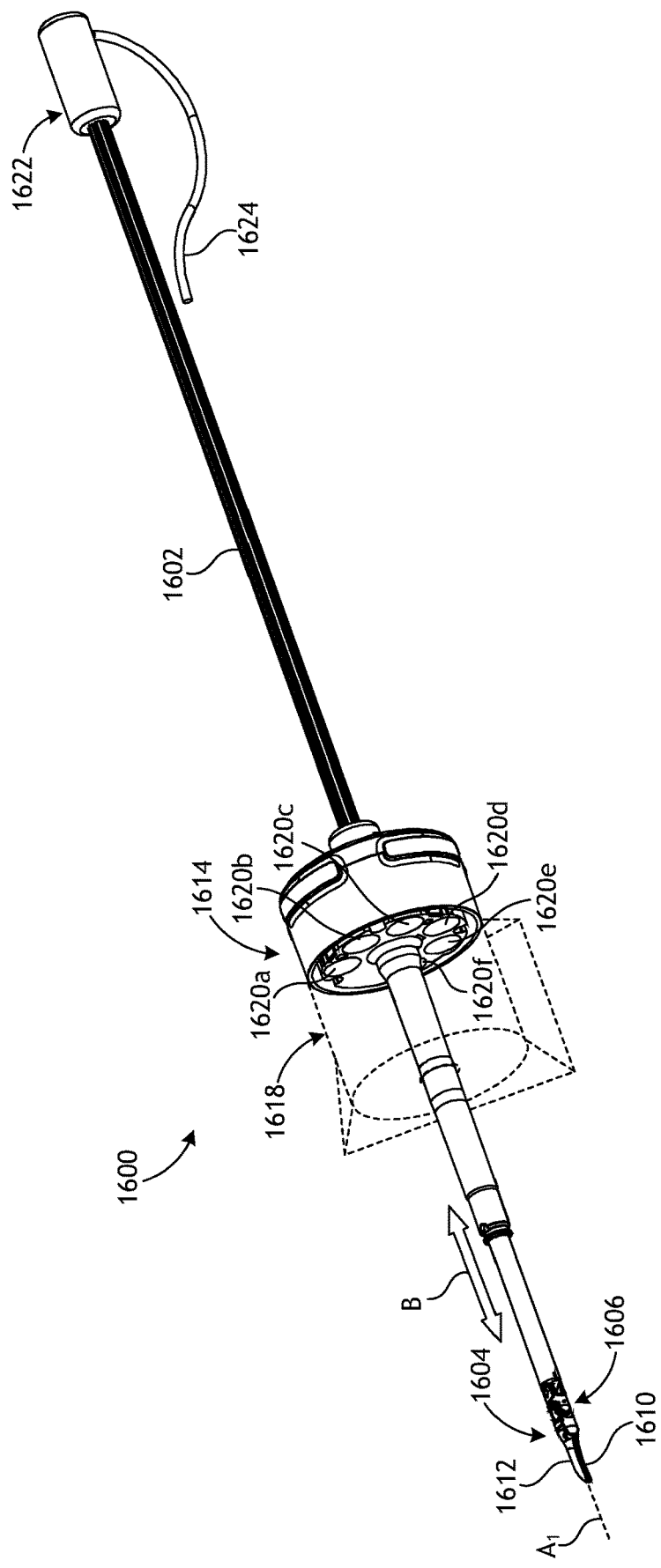
FIG. 16 is an isometric side view of an example surgical tool that may incorporate some or all of the principles of the present disclosure.

FIG. 16 is an isometric side view of an example surgical tool 1600 that may incorporate some or all of the principles of the present disclosure. The surgical tool 1600 may be similar in some respects to any of the surgical tools and medical instruments described above with reference to FIGS. 11-13 and, therefore, may be used in conjunction with a robotic surgical system, such as the robotically-enabled systems 100, 400, and 900 of FIGS. 1-9C. As illustrated, the surgical tool 1600 includes an elongated shaft 1602, an end effector 1604 arranged at the distal end of the shaft 1602, and an articulable wrist 1606 (alternately referred to as a "wrist joint") that interposes and couples the end effector 1604 to the distal end of the shaft 1602. In some embodiments, the wrist 1606 may be omitted, without departing from the scope of the disclosure.

The terms "proximal" and "distal" are defined herein relative to a robotic surgical system having an interface configured to mechanically and electrically couple the surgical tool 1600 to a robotic manipulator. The term "proximal" refers to the position of an element closer to the robotic manipulator and the term "distal" refers to the position of an element closer to the end effector 1604 and thus closer to the patient during operation. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

The surgical tool 1600 can have any of a variety of configurations capable of performing one or more surgical functions. In the illustrated embodiment, the end effector 1604 comprises vessel sealer capable of cutting and cauterizing/sealing tissue or vessels. The end effector 1604 includes opposing jaws 1610, 1612 configured to move (articulate) between open and closed positions. Alternatively, the end effector 1604 may comprise other types of instruments with opposing jaws such as, but not limited to, a surgical stapler, tissue graspers, surgical scissors, clip appliers, needle drivers, a babcock including a pair of opposed grasping jaws, bipolar jaws (e.g., bipolar Maryland grasper, forceps, a fenestrated grasper, etc.), etc. In other embodiments, the end effector 1604 may instead comprise any end effector or instrument capable of being operated in conjunction with the presently disclosed robotic surgical systems and methods, such as a suction irrigator, an endoscope (e.g., a camera), or any combination thereof.

One or both of the jaws 1610, 1612 may be configured to pivot to actuate the end effector 1604 between open and closed positions. In the illustrated example, the jaws 1610, 1612 are bifurcating jaws that simultaneously move to pivot between open (unclamped) and closed (clamped) positions. In other embodiments, however, the second jaw 1612 may be rotatable (pivotable) relative to the first jaw 1610 to actuate the end effector 1604 between the open and closed positions. In yet other embodiments, the first jaw 1610 may move (rotate) relative to the second jaw 1612 to move the jaws 1610, 1612 between the open and closed positions.

The wrist 1606 enables the end effector 1604 to articulate (pivot) relative to the shaft 1602 and thereby position the end effector 1604 at various desired orientations and locations relative to a surgical site. In the illustrated embodiment, the wrist 1606 is designed to allow the end effector 1604 to pivot (swivel) left and right relative to a longitudinal axis $A_1$ of the shaft 1602. In other embodiments, however, the wrist 1606 may be designed to provide multiple degrees of freedom, including one or more translational variables (i.e., surge, heave, and sway) and/or one or more rotational variables (i.e., Euler angles or roll, pitch, and yaw). The translational and rotational variables describe the position and orientation of a component of a surgical system (e.g., the end effector 1604) with respect to a given reference Cartesian frame. "Surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The end effector 1604 is depicted in FIG. 16 in the unarticulated position where the longitudinal axis of the end effector 1604 is substantially aligned with the longitudinal axis $A_1$ of the shaft 1602, such that the end effector 1604 is at a substantially zero angle relative to the shaft 1602. In the articulated position, the longitudinal axis of the end effector 1604 would be angularly offset from the longitudinal axis $A_1$ such that the end effector 1604 would be oriented at a non-zero angle relative to the shaft 1602.

Still referring to FIG. 16, the surgical tool 1600 may include a drive housing or "handle" 1614, and the shaft 1602 extends longitudinally through the handle 1614. The handle 1614 houses an actuation system designed to move the shaft 1602 relative to the handle 1614, and further designed to facilitate articulation of the wrist 1606 and actuation (operation) of the end effector 1604 (e.g., clamping, firing, rotation, articulation, energy delivery, etc.). More specifically, the systems and mechanisms housed within the handle 1614 are actuatable to move (translate) a plurality of drive members that extend along at least a portion of the shaft 1602, either on the exterior or within the interior of the shaft 1602. Example drive members include, but are not limited to, cables, bands, lines, cords, wires, woven wires, ropes, strings, twisted strings, elongate members, belts, shafts, flexible shafts, drive rods, or any combination thereof. The drive members can be made from a variety of materials including, but not limited to, a metal (e.g., tungsten, stainless steel, nitinol, etc.) a polymer (e.g., ultra-high molecular weight polyethylene), a synthetic fiber (e.g., KEVLAR®, VECTRAN®, etc.), an elastomer, or any combination thereof.

Selective actuation of one or more of the drive members, for example, may cause the shaft 1602 to translate relative to the handle 1614 in z-axis translation, as indicated by the arrows B, and thereby advance or retract the end effector 1602. Selective actuation of one or more other drive members may cause the end effector 1604 to articulate (pivot) relative to the shaft 1602 at the wrist 1606. Selective actuation of one or more additional drive members may cause the end effector 1604 to actuate (operate). Actuating the end effector 1604 depicted in FIG. 16 may entail closing and/or opening the jaws, 1610, 1612 and thereby enabling the end effector 1604 to grasp (clamp) onto tissue. Once tissue is grasped or clamped between the opposing jaws 1610, 1612, actuating the end effector 1604 may further include "firing" the end effector 1604, which may refer to causing a cutting element or knife (not visible) to advance distally within a slot or "guide track" defined in the first jaw 1610. As it moves distally, the knife transects any tissue grasped between the opposing jaws 1610, 1612. Actuating the end effector 1604 may further entail triggering energy delivery (e.g., RF energy) to cauterize and/or seal tissue or vessels grasped between the jaws 1610, 1612.

The handle 1614 provides or otherwise includes various coupling features that releasably couple the surgical tool 1600 to an instrument driver 1618 (shown in dashed lines) of a robotic surgical system. The instrument driver 1618 may be similar in some respects to the instrument drivers 1102, 1200 of FIGS. 11 and 12, respectively, and therefore may be best understood with reference thereto. Similar to the instrument drivers 1102, 1200, for example, the instrument driver 1618 may be mounted to or otherwise positioned at the end of a robotic arm (not shown) and is designed to provide the motive forces required to operate the surgical tool 1600. Unlike the instrument drivers 1102, 1200, however, the shaft 1602 of the surgical tool 1600 extends through and penetrates the instrument driver 1618.

The handle 1614 includes one or more rotatable drive inputs matable with one or more corresponding drive outputs (not shown) of the instrument driver 1618. Each drive input is actuatable to independently drive (actuate) the systems and mechanisms housed within the handle 1614 and thereby operate the surgical tool 1600. In the illustrated embodiment, the handle 1614 includes a first drive input 1620*a*, a second drive input 1620*b*, a third drive input 1620*c*, a fourth drive input 1620*d*, a fifth drive input 1620*e*, and a sixth drive input 1620*f* (mostly occluded). While six drive inputs 1620*a-f* are depicted, more or less than six may be included in the handle 1614 depending on the application, and without departing from the scope of the disclosure.

Each drive input 1620*a-f* may be matable with a corresponding drive output (not shown) of the instrument driver 1618 such that movement (rotation) of a given drive output correspondingly moves (rotates) the associated drive input 1620*a-f* and thereby causes various operations of the surgical tool 1600. Example operations that may be triggered by actuating the drive inputs 1620*a-f* include, but are not limited to, causing the knife to fire at the end effector 1604 (e.g., advancing or retracting the knife), causing the shaft 1602 to move (translate) relative to the handle 1614 along the longitudinal axis $A_1$, locking or unlocking z-axis translation of the shaft 1602, causing articulation of the end effector 1604 at the wrist 1606, and causing the jaws 1610, 1612 to open or close.

In some embodiments, the surgical tool 1600 may further include a proximal housing or "tailpiece" 1622 arranged at the proximal end of the shaft 1602. Some or all of the drive members extending along the shaft 1602 may terminate and be anchored at the tailpiece 1622. In other embodiments, one or more of the drive members may loop around a pulley or similar return feature within the tailpiece 1622 and thereby extend along the shaft 1602 in both directions.

In some embodiments, the surgical tool 1600 may be supplied with electrical power (current) via a power cable 1624 coupled to the tailpiece 1622. In other embodiments, the power cable 1624 may be omitted and electrical power may be supplied to the surgical tool 1600 via an internal power source, such as one or more batteries or fuel cells. In such embodiments, the surgical tool 1600 may alternatively be characterized and otherwise referred to as an "electrosurgical instrument" capable of providing electrical energy to the end effector 1604. The power cable 1624 may place the surgical tool 1600 in communication with a generator (not shown) that supplies energy, such as electrical energy (e.g., radio frequency energy), ultrasonic energy, microwave energy, heat energy, or any combination thereof, to the surgical tool 1600 and, more particularly, to the end effector 1604.

Figure 17:
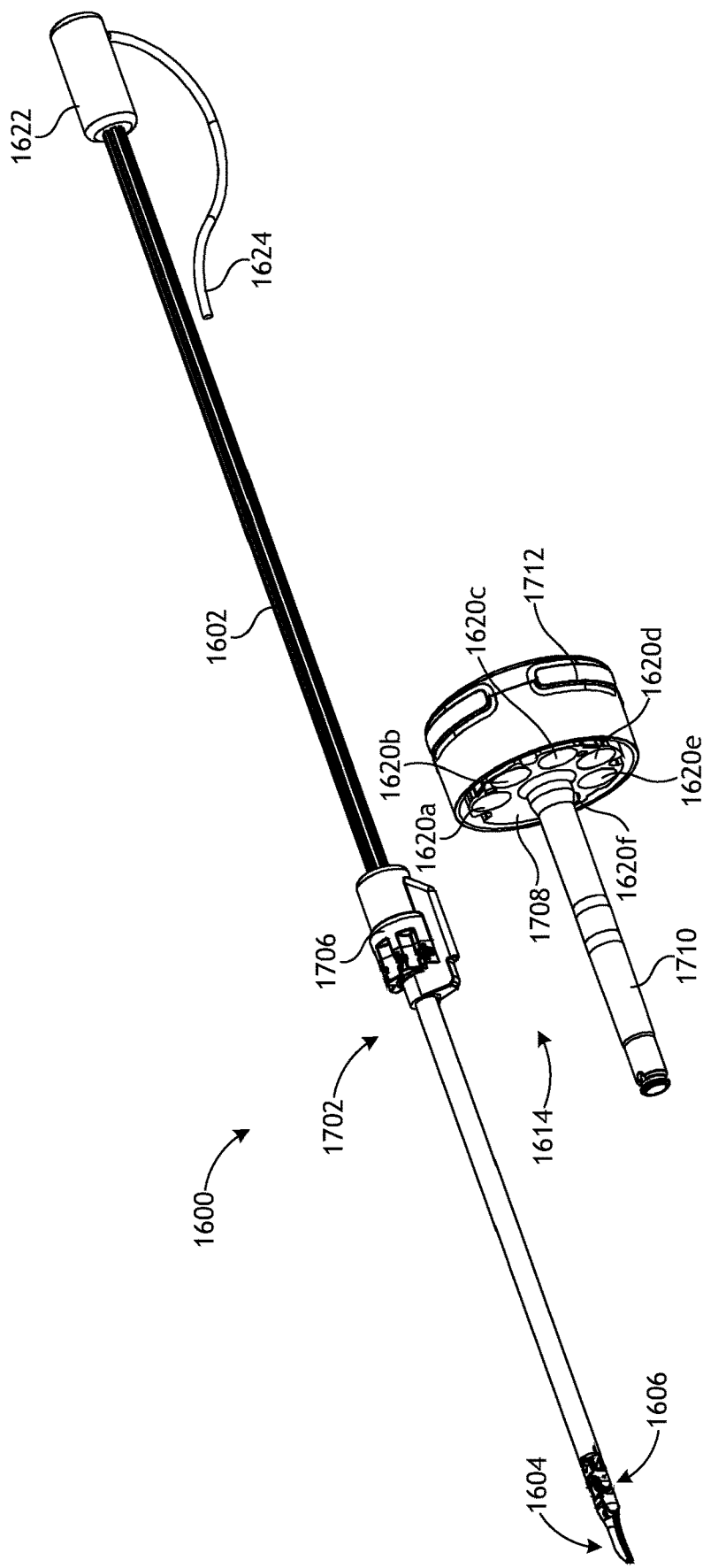
FIG. 17 is an exploded isometric view of the surgical tool of FIG. 16, according to one or more embodiments.

FIG. 17 is an exploded isometric view of the surgical tool 1600, according to one or more embodiments. Surgical instruments are complex devices with high part counts, which contributes to elevated tool costs. This can be particularly problematic for single-use disposable surgical instruments. According to embodiments of the present disclosure, the surgical tool 1600 provides a means to mitigate the high cost of surgical instruments by including disposable and reusable parts or assemblies, which enables business objectives to be met. As illustrated, for example, the surgical tool 1600 may include a first "disposable" assembly 1702 and a second or "reusable" assembly 1704, where the two assemblies are matable and otherwise able to be combined (assembled together) to form the surgical tool 1600. The first assembly 1702 may be disposable and otherwise decommissioned following a predetermined number of uses, while the more complex second assembly 1704 may be reusable and operated until exhausting its operating lifespan.

In the illustrated embodiment, the first assembly 1702 includes at least the shaft 1602, the end effector 1604, the drive members (not clearly visible in FIG. 17), a center housing 1706, the tailpiece 1622, and the power cable 1624. In some applications, the wrist 1606 may also be included in the first assembly 1702, but could be omitted in tools where no wrist is required. In this embodiment and others, the power cable 1624 may be reusable and separable from the first assembly 1702, allowing additional cost savings to be realized, without departing from the scope of this disclosure. In contrast, the second assembly 1704 includes more complex machinery and devices that help operate the surgical tool 1600. In the illustrated embodiment, the second assembly 1704 includes a handle housing 1708, an alignment nozzle 1710 extending distally from the handle housing 1708, the drive inputs 1620*a-f*, a bailout ring 1712, and a plurality of input stacks (not visible) arranged within the bailout ring 1712. One skilled in the art will appreciate that the power cable 1624 may alternatively be permanently attached or separable from the second assembly 1704 to achieve the same objective of reducing the cost of the single use assembly.

To assemble the surgical tool 1600, the end effector 1604 and the shaft 1602 are extended through the bailout ring 1712 and the handle housing 1708, and advanced further to extend through the alignment nozzle 1710. The center housing 1706 may be received by and matable with the handle housing 1708 within the bailout ring 1712. The center housing 1706, the handle housing 1708, the drive inputs 1620*a-f*, the bailout ring 1712, and the plurality of input stacks arranged within the bailout ring 1712 collectively form or provide the handle 1614, as generally described above. The center housing 1706 may be slidable (translatable) along the length of the shaft 1602 during operation, thus allowing the handle 1614 to translate in z-axis translation.

The alignment nozzle 1710 may include various alignment features that help align the surgical tool 1600 with the instrument driver 1618 (FIG. 16) in a proper angular orientation. Properly aligning the surgical tool 1600 with the instrument driver 1618 allows the drive inputs 1620*a-f* to align and mate with corresponding drive outputs provided by the instrument driver 1618. Once properly mated, the drive inputs 1620*a-f* will share axes of rotation with the corresponding drive outputs to allow the transfer of rotational torque from the drive outputs to the corresponding drive inputs 1620*a-f*.

Figure 18:
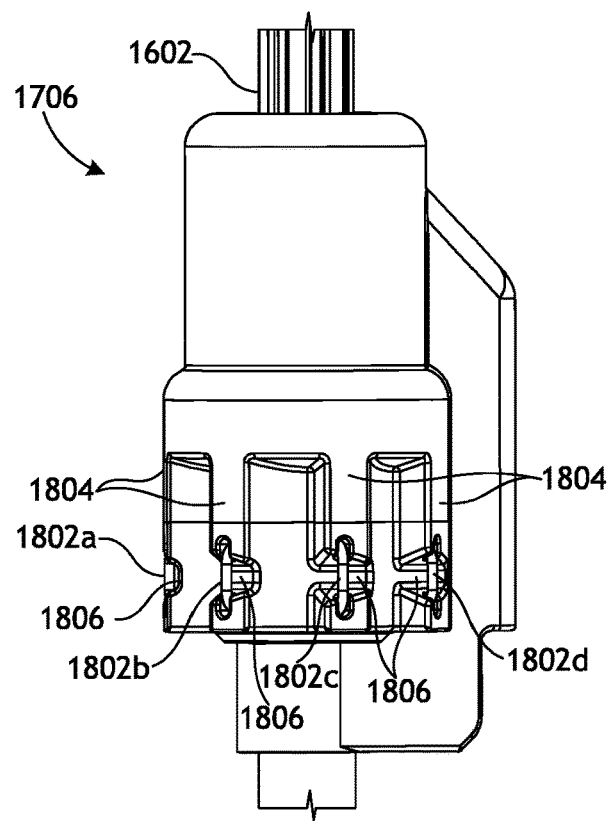
FIG. 18 is an enlarged side view of the center housing of FIG. 17, according to one or more embodiments.

FIG. 18 is an enlarged side view of the center housing 1706, according to one or more embodiments. The center housing 1706 may be configured to receive and redirect drive members to and from the shaft 1602 to be accessible for capture and actuation. In the illustrated embodiment, small portions (segments) of a first drive member 1802*a*, a second drive member 1802*b*, a third drive member 1802*c*, and a fourth drive member 1802*d* are visible, while the remaining portions extend to/from the shaft 1602 within the center housing 1706 and along the length of the shaft 1602. The drive members 1802*a-d* may comprises a cable or wire and, therefore, may be referred to as "drive cables". In other embodiments, however, the drive members 1802*a-d* may comprise any of the other types of drive members mentioned herein. While four drive members 1802*a-d* are depicted, more than four may be included, without departing from the scope of the disclosure. In at least one embodiment, for example, the number of drive members 1802*a-d* may be the same as the number of drive inputs 1620*a-f* (FIGS. 16-17).

The drive members 1802*a-d* extend along at least a portion of the shaft 1602. As illustrated, the center housing 1706 may provide or otherwise define a plurality of lateral flanges 1804. The lateral flanges 1804 extend radially outward from the body of the center housing 1706 and are angularly offset from each other about the outer circumference of the center housing. Each lateral flange 1804 may be configured to accommodate and expose a portion (segment) of one of the drive members 1802*a-d*. More specifically, each lateral flange 1804 defines a notch 1806, and the drive member 1802*a-d* for each flange 1804 extends across (over) the notch 1806, which provides a location where the drive member 1802*a-d* may be located and captured (i.e., picked up), as described in more detail below. In at least one embodiment, as illustrated, the notches 1806 may be aligned in a common plane perpendicular to the axis of shaft 1602, thus exposing the drive members 1802*a-d* in the common plane. In other embodiments, however, the notches 1806 may reside in more than one plane, without departing from the scope of this disclosure. Likewise, the center axis of each exposed portion of drive member 1820*a-d* may be arranged radially in a pattern of equal or unequal spacing about the shaft 1602, without departing from the scope of this disclosure.

Figure 19:
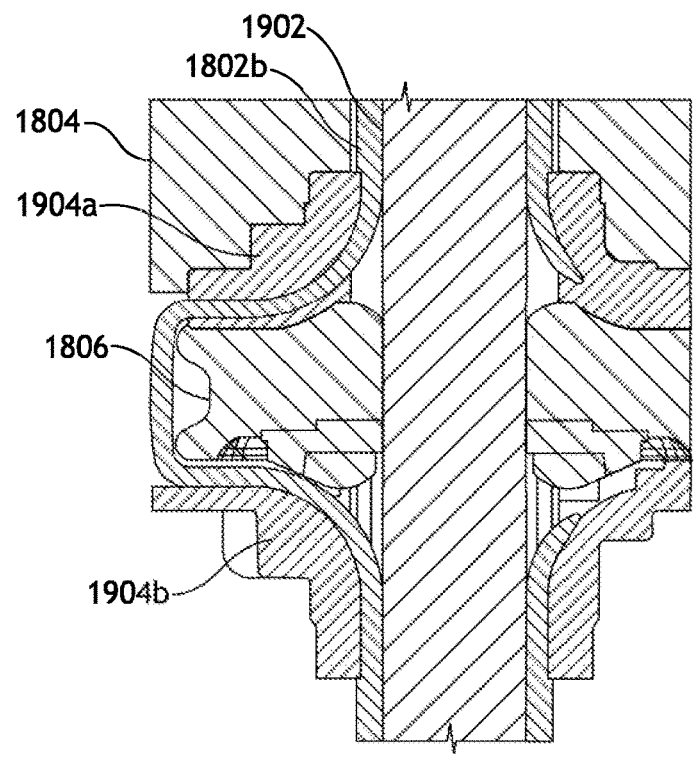
FIG. 19 is a cross-sectional side view of a portion of the center housing of FIG. 18, according to one or more embodiments.

FIG. 19 is a cross-sectional side view of a portion of the center housing 1706, according to one or more embodiments. As illustrated, the second drive member 1802*b* is depicted as extending along the shaft 1602 within the center housing 1706. While the following discussion is directed to the second drive member 1802*b*, the discussion is equally applicable to any of the drive members 1802*a-d* of FIG. 18. As illustrated, the drive member 1802*b* may be received and extend within a groove 1902 defined in the shaft 1602. In other embodiments, however, the drive member 1802*b* may alternatively be received within the interior of the shaft 1602 or extend along an exterior surface of the shaft 1602, without departing from the scope of the disclosure.

The center housing 1706 may redirect the drive member 1802*b* away from and back to the shaft 1602 at the location of the lateral flange 1804. More specifically, the center housing 1706 may include first ("upper") and second ("lower") redirect features 1904*a* and 1904*b* that redirect the drive member 1802*a,b* to the lateral flange 1804. At the lateral flange 1804, the drive member 1802*b* extends out of the center housing 1706 and across the notch 1806. The notch 1806 provides a location where the drive member 1802*b* can be captured and otherwise grasped onto, as described in more detail below.

The redirect features 1904*a,b* may comprise any structure or mechanism capable of redirecting the drive member 1802*b* to and/or from the shaft 1602. In some embodiments, one or both of the redirect features 1904*a,b* may form an integral part of the center housing 1706, but may alternatively comprise separate component parts mounted to the center housing 1706. In the illustrated embodiment, the redirect features 1904*a,b* comprise static redirect features that cradle the drive member 1802*b*, and the drive member 1802*b* is configured to slide against (along) the static surfaces during translation (operation). In other embodiments, however, one or both of the redirect features 1904*a,b* may comprise a pulley or other rotating structure that rolls with movement of the drive member 1802*b*, without departing from the scope of the disclosure.

Figure 20:
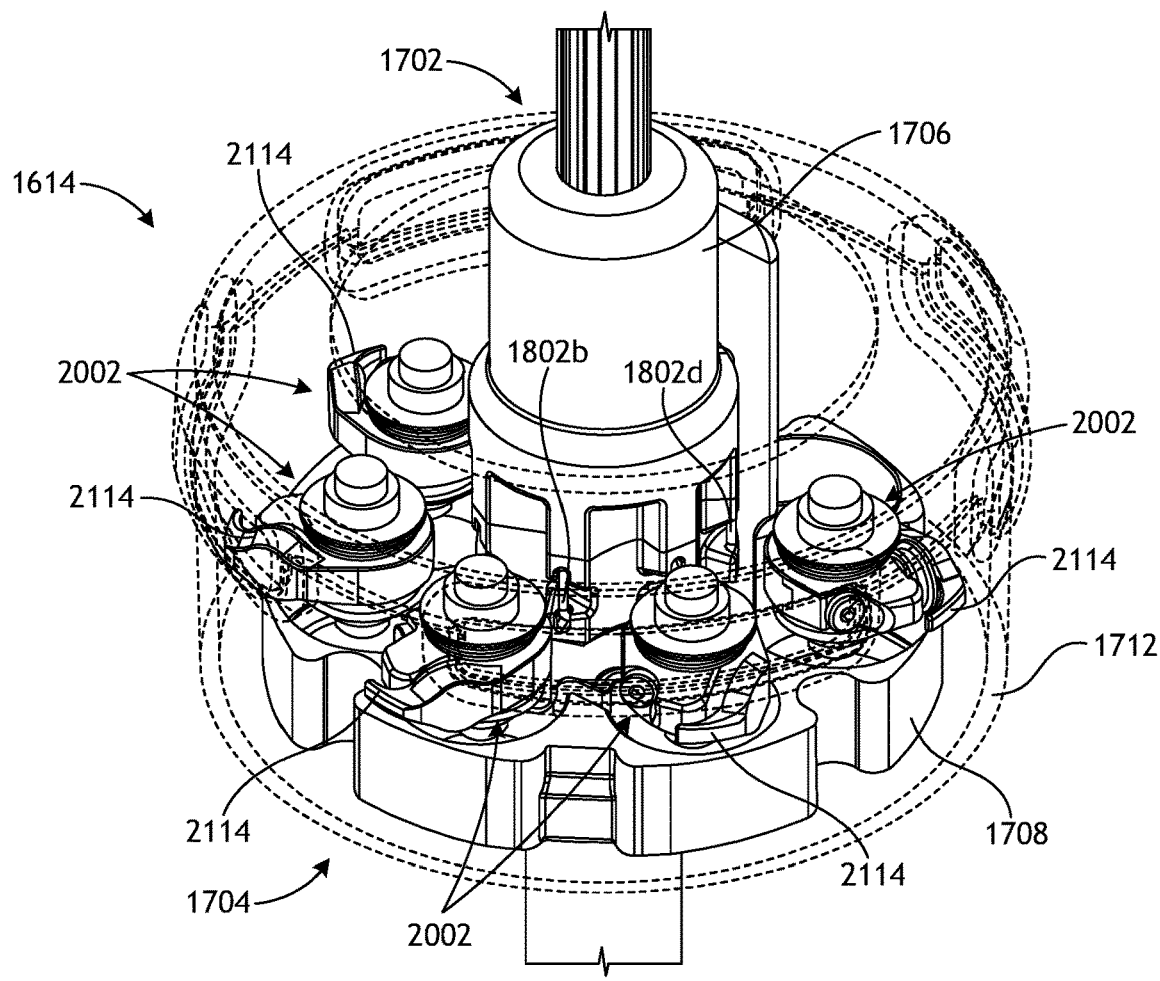
FIG. 20 is an isometric view of the handle of FIGS. 16-17, according to one or more embodiments.

FIG. 20 is an isometric view of the handle 1614, according to one or more embodiments. More specifically, FIG. 20 shows the first and second assemblies 1702, 1704 mated and otherwise combined to form the handle 1614. The bailout ring 1712 is shown in phantom (dashed lines) in FIG. 20 to allow viewing of the internal component parts of the handle 1614.

The handle 1614, and more particularly, the second assembly 1704, may include a plurality of input stacks 2002 arranged within the bailout ring 1712. While five input stacks 2002 are depicted in FIG. 20, more or less than five may be included in the handle 1614. In at least one embodiment, the number of input stacks 2002 may be the same as the number of drive inputs 1620*a-f* (FIGS. 16-17). Each input stack 2002 may be operatively coupled to a corresponding one of the drive inputs 1602*a-f* such that actuation of a given drive input 1602*a-f* will actuate (e.g., rotate) the corresponding input stack 2002 coupled thereto.

Figure 21:
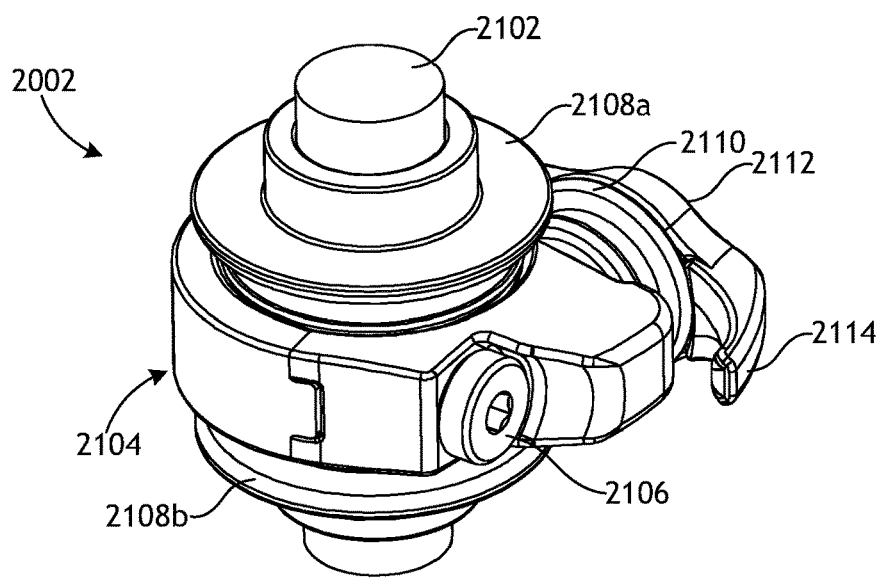
FIG. 21 is an enlarged, isometric side view of an example input stack from FIG. 20, according to one or more embodiments.

Referring briefly to FIG. 21, depicted is an enlarged, isometric side view of an example input stack 2002, according to one or more embodiments. As illustrated, the input stack 2002 includes a drive shaft 2102 and an armature 2104 coupled to or forming part of the drive shaft 2102. The drive shaft 2102 may be coupled to or form part of the one of the drive inputs 1620*a-f* (FIGS. 16-17) such that rotation of the drive input 1620*a-f* correspondingly rotates the drive shaft 2102 and simultaneously rotates the armature 2104 in the same angular direction.

In some embodiments, the armature 2104 may be mechanically attached to the drive shaft 2102. In such embodiments, as illustrated, the armature 2104 may comprise a type of clamping assembly made of two or more component parts mechanically fastened to the drive shaft 2102 using one or more mechanical fasteners 2106. In other embodiments, however, the armature 2104 may be overmolded onto the drive shaft 2102, or may alternatively be secured thereto by an interference (press) fit, welding, brazing, or through the use of an adhesive. In yet other embodiments, the armature 2104 may form an integral part or extension of the drive shaft 2102, without departing from the scope of the disclosure.

As illustrated, the armature 2104 may interpose a first or "upper" spooling pulley 2108a and a second or "lower" spooling pulley 2108b. The upper and lower spooling pulleys 2108a,b may be rotatably mounted to the drive shaft 2102 and axially offset from each other, thus sharing the same axis of rotation. The armature 2104 may further include a winding pulley 2110 laterally offset from the upper and lower spooling pulleys 2108a,b. The winding pulley 2110, for example, may be rotatably mounted to a lateral arm 2112 extending from the armature 2104.

The input stack 2002 may further provide or otherwise define a drive member engagement device 2114 coupled to or extending from the armature 2104 and, more specifically, from the lateral arm 2112. The drive member engagement device 2114 may comprise a feature or structure capable of locating and capturing a corresponding drive member 1802a-d (FIG. 18) and feeding the drive member 1802a-d to the winding pulley 2110 as the input stack 2002 rotates. In the illustrated embodiment, the drive member engagement device 2114 comprises a hook or hook member extending from the lateral arm 2112, but could alternatively comprise another suitable structure or feature.

In one or more embodiments, one or more of the spooling pulleys 2108a,b and the winding pulley 2110 may be comprise or may otherwise be replaced with a static redirect feature. In such embodiments, the drive members 1802a-d (FIG. 18) may be configured to slide against the static surfaces of the static redirect features during translation (operation).

Referring again to FIG. 20, upon mating the first and second assemblies 1702, 1704 to form the handle 1614, the input stacks 2002 will be oriented such that the drive member engagement devices 2114 are positioned radially outward and otherwise at an angular orientation that does not impede insertion and mating of the central housing 1706 with the handle housing 1708. In some embodiments the input stacks 2002 may be naturally biased away from the center of the handle 1614 (e.g., with a torsion spring or the like) such that the drive member engagement devices 2114 do not impede mating.

Once the central housing 1706 is properly mated with the handle housing 1708, and the handle 1614 is mounted to the instrument driver 1618 (FIG. 16), the drive inputs 1602a-f (FIGS. 16-17) may be actuated to rotate the input stacks 2002 to locate and capture a corresponding one of the drive members 1802a-d with the associated drive member engagement device 2114 (in FIG. 20, only the second and fourth drive members 1802b,d are visible). This "homing" process threads the drive members 1802a-d onto respective input stacks 2002 and thereby places the surgical tool 1600 (FIGS. 16-17) in condition for operation.

Figure 22A:
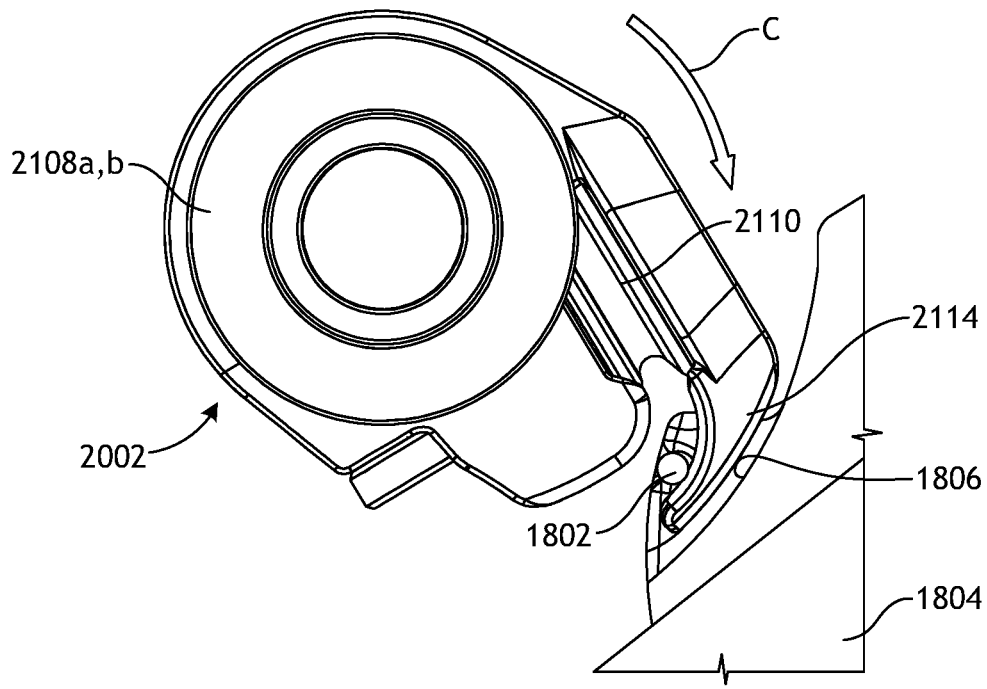
FIGS. 22A and 22B are enlarged views of an example input stack from FIG. 20 during a homing process, according to one or more embodiments.
Figure 22B:
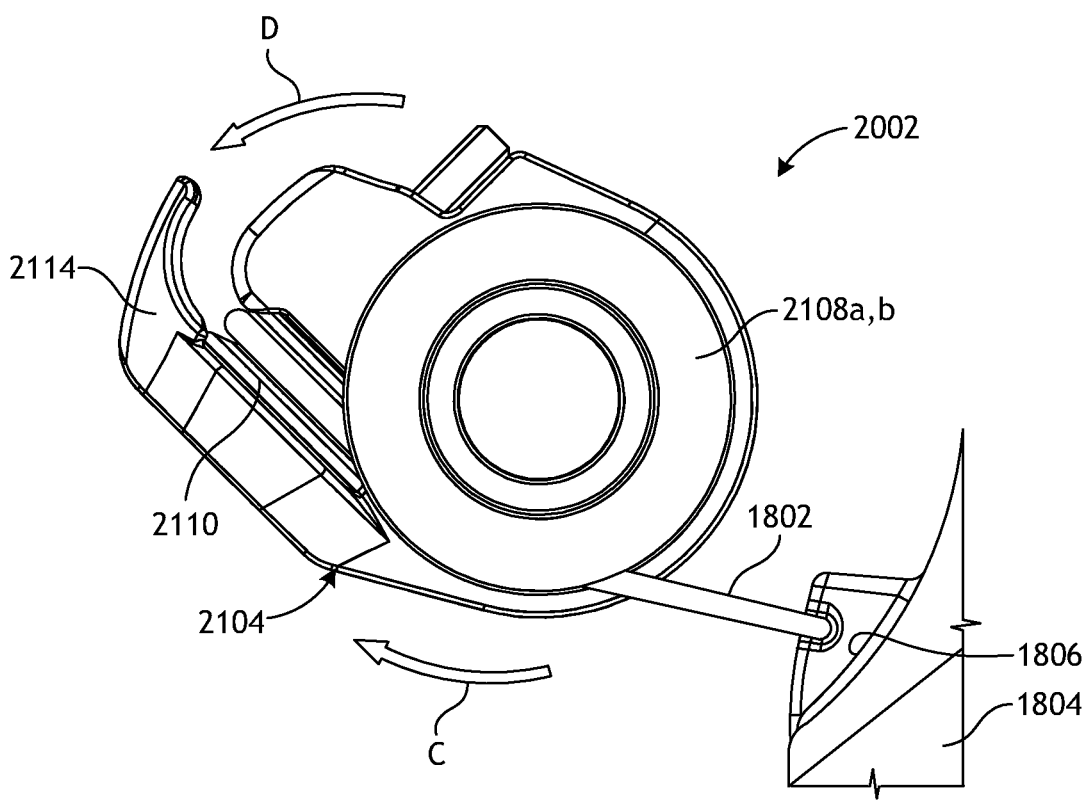

FIGS. 22A and 22B are enlarged views of an example input stack 2002 and depict progressive views during the homing process, according to one or more embodiments. In FIG. 22A, upon rotating the input stack 2002 in a first angular direction C (e.g., clockwise), the drive member engagement device 2114 may be configured to traverse the notch 1806 of the corresponding lateral flange 1804 and thereby locate and capture the drive member 1802 extending across (over) the notch 1806. Accordingly, the drive member engagement device 2114 may be arranged and sized to enter and traverse the notch 1806 as the input stack 2002 rotates in the first angular direction C.

In FIG. 22B, once the drive member engagement device 2114 engages and captures the drive member 1802, further rotation of the input stack 2002 the first angular direction C will effectively thread the drive member 1802 onto the input stack 2002. More specifically, as the input stack 2002 rotates, the drive member 1802 will eventually be received into the winding pulley 2110, and further rotation of the input stack 2002 will route the drive member 1802 around the upper and lower spooling pulleys 2108a,b from the winding pulley 2110. During the homing process, the input stack 2002 may be rotated until a predetermined tension is achieved in the drive member 1802, thus ensuring accurate antagonistic control of the end effector 1604 (FIGS. 16-17) during operation. In some embodiments, the input stack 2002 may be rotated until cable tensioning members (not shown) that prevent off robot derailment have been compressed to a hard stop.

Once the input stack 2002 is properly homed, the upper spooling pulley 2108a may be arranged and otherwise configured to convey the drive member 1802 to/from the upper redirect feature 1904a (FIG. 19), and the lower spooling pulley 2108a may be arranged and otherwise configured to convey the drive member 1802 to/from the lower redirect feature 1904b (FIG. 19). The winding pulley 2110 may be arranged to receive and redirect the drive member 1802 between the upper and lower spooling pulleys 2108a,b. More specifically, in some embodiments, the upper and lower spooling pulleys 2108a,b may be arranged for rotation in respective parallel planes, while the winding pulley 2110 may be arranged for rotation in a plane that is 90° offset from the parallel planes in order to redirect the drive member 1802 between the upper and lower spooling pulleys 2108a,b. In one embodiment, for example, the parallel planes of the upper and lower spooling pulleys 2108a,b may be characterized as extending substantially horizontal, and the plane of the winding pulley 2110 may be characterized as extending substantially vertical and otherwise 90° offset from the horizontal planes. In other embodiments, however, the planes of the upper and lower spooling pulleys 2108a,b and the winding pulley 2110 need not be 90° offset from each other. Moreover, the upper and lower spooling pulleys 2108a,b need not be arranged for rotation in respective parallel planes, but may alternatively be arranged in non-parallel planes, without departing from the scope of the disclosure.

During operation, the input stack 2002 may be actuated or operated by rotating the corresponding drive input 1620a-f (FIGS. 16-17). Rotating the corresponding drive input 1620a-f in the first angular direction C will correspondingly rotate the drive shaft 2102 and the armature 2104 in the same direction and about the same rotational axis. Because the drive member 1802 is anchored to the shaft 1602 (FIGS. 16-17) at or near the tailpiece 1602, the drive member 1802 may be drawn (pulled) into the armature 2104 as the armature 2104 rotates in the first direction C. Upon releasing the torque at the corresponding drive input 1620a-f, or otherwise reversing the direction of the corresponding drive input 1620a-f, the drive shaft 2102 and the armature 2104 will rotate in a second angular direction D (e.g., counter-clockwise) opposite the first angular direction C, and a length of the drive member 1802 may correspondingly be paid out (fed) to the shaft 1602.

As briefly mentioned above, manipulating the drive member 1802 by actuating the drive stack 2002 may cause the surgical tool 1600 (FIG. 16) to undertake one or more operations. More specifically, manipulating the drive member 1802 cause the jaws 1610, 1612 (FIGS. 16-17) at the end effector 1604 (FIG. 16) to open and close. In other embodiments, however, manipulating the drive member 1802 may cause the end effector 1604 (FIGS. 16-17) to articulate, or cause the end effector 1604 to "fire," without departing from the scope of this disclosure.

In some embodiments, the input stack 2002 may be decoupled from the shaft 1602 (FIGS. 16-17) insertion. More specifically, the spooling pulleys 2108*a,b* and the winding pulley 2110 may be able to freely rotate (e.g., "free wheel") and are otherwise not driven during operation of the handle 1614 (FIGS. 16-17 and 20). Consequently, as the shaft 1602 moves longitudinally relative to the handle 1614 in z-axis translation, the drive member 1802 is able to freely run (course) through the armature 2104 between the spooling pulleys 2108*a,b*. Moreover, since the spooling pulleys 2108*a-c* and the winding pulley 2110 are able to freely rotate, the input stack 2002 can be operated simultaneously during shaft 1602 translation.

In assembling the handle 1614 (FIG. 20), the first assembly 1702 (FIG. 20) may be mated with and locked into the second assembly 1704 (FIG. 20) by a spring loaded latching mechanism (not shown), for example. Alternatively, or in addition thereto, the first assembly 1702 may be joined to the second assembly 1704 as a result of the homing process described above. More specifically, the armature 2104 of one or more of the input stacks 2002 may be oriented to radially extend into and intersect the corresponding groove 1806 once the drive member 1802 has been picked up and directed to the spooling pulley 2110. A radially extended armature 2104 occupying the groove 1806 may be able to assume any surge loads applied along the axis of the shaft 1602 (FIG. 20) during instrument operation.

Self-Winding Cable Instrument—Bailout

Figure 23:
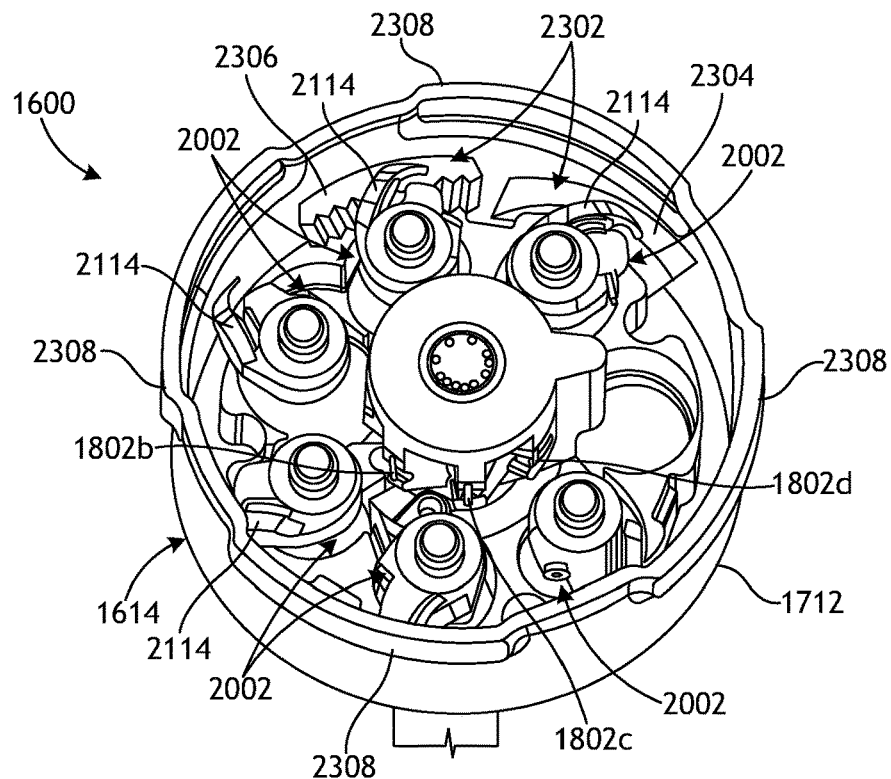
FIG. 23 is a cross-sectional top view of the surgical tool of FIGS. 16-17 taken at the handle, according to one or more embodiments.

FIG. 23 is a cross-sectional top view of the surgical tool 1600 taken through the handle 1614, according to one or more embodiments. In some embodiments, the handle 1614 may be manually actuatable to bail out the surgical tool 1600 from various operations or configurations. Manually bailing out the surgical tool 1600 may be required in the event power to the surgical tool 1600 is lost or the surgical tool 1600 is otherwise rendered inoperable.

As described herein, bailing out the surgical tool 1600 may entail preparing the surgical tool 1600 to allow the first assembly 1702 (FIG. 17) to be decoupled from the second assembly 1704 (FIG. 17). The handle 1614 may include one or more decoupling mechanisms 2302 defined or otherwise provided on the inner circumferential surface of the bailout ring 1712. As the bailout ring 1712 is manually rotated about a central axis, the decoupling mechanism(s) 2302 may be configured to act on the inputs stacks 2002 and disengage the drive member engagement device 2114 of each input stack 2002 from the corresponding drive members 1802*a-d*. Once the drive member engagement devices 2114 are rotated out of engagement with the drive members 1802*a-d*, the first assembly 1702 may then be decoupled from the second assembly 1704 without the drive member engagement devices 2114 impeding retraction movement of the first assembly 1702.

In one or more embodiments, as illustrated, the decoupling mechanism 2302 may comprise one or more ramped features 2304 (one shown) defined on the inner circumferential surface of the bailout ring 1712 and extending radially inward. While one ramped feature 2304 is depicted, more than one may be included on the inner circumferential surface of the bailout ring 1712. As the bailout ring 1712 is rotated, the ramped feature 2304 may be configured to engage and lift (vertically) one or more of the input stacks 2002 until they are decoupled from their corresponding drive inputs 1620*a-f* (FIGS. 16-17). In some embodiments, once decoupled from the corresponding drive inputs 1620*a-f*, the input stacks 2002 may naturally rotate to a disengaged orientation and otherwise disengage the corresponding drive member engagement device 2114 from the corresponding drive member 1802*a-d*. In such embodiments, the input stacks 2002 may be naturally biased to the disengaged orientation, such as with a torsion spring or the like.

In other embodiments, the decoupling mechanism 2302 may further include a ring gear 2306 defined on all or a portion of the inner circumferential surface of the bailout ring 1712. While one ring gear 2306 is depicted, more than one may be included on the inner circumferential surface of the bailout ring 1712. As the bailout ring 1712 is rotated, the ring gear 2306 may be configured to locate and engage a corresponding pinion gear (not shown) provided on the input stacks 2002. Further rotation of the bailout ring 1712 will cause the ring gear 2306 to drive the pinion gear and thereby rotate the input stacks to the disengaged orientation and otherwise out of engagement with the corresponding drive members 1802*a-d*.

In some embodiments, the outer periphery (circumference) of the bailout ring 1712 may provide or otherwise define a gripping interface 2308 to help enable a user to grasp and rotate the bailout ring 1712. In the illustrated embodiment, the gripping interface 2308 comprises one or more arcuate projections extending radially outward from the outer periphery (circumference) of the bailout ring 1712, but could alternatively comprise any other feature or structure that may be gripped or grasped by a user to manually manipulate the bailout ring 1712 (e.g., rotating or axially moving the bailout ring 1712).

Self-Winding Cable Instrument—Insertion

Figure 24:
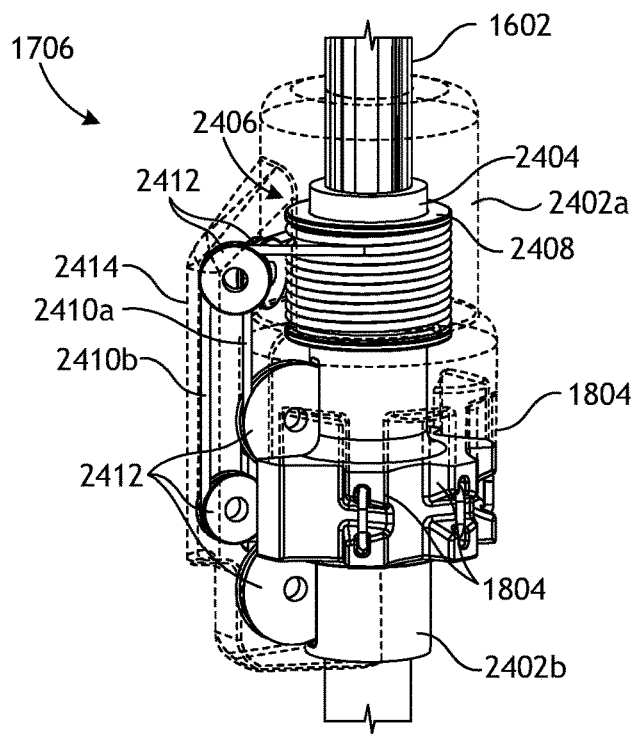
FIG. 24 is an isometric side view of the center housing of FIGS. 17-18, according to one or more embodiments.

FIG. 24 is an isometric side view of the center housing 1706, according to one or more embodiments. In some embodiments, as illustrated, the center housing 1706 may comprise two component parts that are assembled or otherwise matable to form the center housing 1706. More specifically, the center housing 1706 may include a first or "upper" portion 2402*a* and a second or "lower" portion 2402*b* matable with the first portion 2402*b*. The first portion 2402*a* is depicted in FIG. 24 in phantom (dashed lines) to enable viewing of various internal components of the center housing 1706. In at least one embodiment, the lateral flanges 1804 extending laterally from the side of the center housing 1706 are provided by a combination of both the first and second portions 2402*a,b*, but could alternatively be provided entirely by either one of the portions 2402*a,b* independently.

In the illustrated embodiment, the second portion 2402*b* may provide or otherwise define an inner cylindrical extension 2404 that extends proximally. In assembling the center housing 1706, the inner cylindrical extension 2404 may be received within an interior of the first portion 2402*a*. An insertion subsystem 2406 may also be arranged within the interior of the first portion 2402*a* and portions of the insertion subsystem 2406 may be mounted to the inner cylindrical extension 2404. The insertion subsystem 2406 may be actuatable and otherwise operable to cause z-axis translation of the shaft 1602 relative to the center housing 1706, and thereby advance or retract the end effector 1614 (FIGS. 16-17) during operation.

As illustrated, the insertion subsystem 2406 may include an insertion spool 2408 rotatably mounted to the inner cylindrical extension 2404. When the first assembly 1702 (FIG. 17) is mated with the second assembly 1704 (FIG. 17), the insertion spool 2408 may be operatively coupled to one of the drive inputs 1620a-f such that rotation (actuation) of the corresponding drive input 1620a-f causes the insertion spool 2408 to rotate about the inner cylindrical extension 2404. While not shown in FIG. 24, example drive components extending between the insertion spool 2408 and the corresponding drive input 1620a-f that may be actuated to cause the insertion spool 2408 to rotate include, but are not limited to, one or more of a shaft, a gear, a spline, a toothed belt, a friction drive, or any combination thereof.

The insertion subsystem 2406 may further include a first or "upper" drive cable 2410a and a second or "lower" drive cable 2410b. The first and second drive cables 2410a,b may be similar to any of the drive members mentioned herein and may be made of similar materials. The first and second drive cables 2410a,b may be wrapped one or more times around the insertion spool 2408, and rotating the insertion spool 2408 may draw the first and second drive cables 2410a,b into the insertion spool 2408 from the shaft 1602 or alternatively dispense the first and second drive cables 2410a,b from the insertion spool 2408 to the shaft 1602 depending on the rotational direction of the insertion spool 2408. Drawing the first and second drive cables 2410a,b into the insertion spool 2408 from the shaft 1602 is referred to herein as "paying in" (or any grammatical variation thereof), and dispensing the first and second drive cables 2410a,b from the insertion spool 2408 to the shaft 1602 is referred to herein as "paying out" (or any grammatical variation thereof).

The first drive cable 2410a may extend proximally from the insertion spool 2408 and may be anchored to the shaft 1602 at or near a proximal end of the shaft 1602 or otherwise proximal to the center housing 1706. In contrast, the second drive cable 2410b may extend distally from the insertion spool 2408 and may be anchored to the shaft 1602 at or near a distal end of the shaft 1602 or otherwise distal to the center housing 1706. In the illustrated embodiment, the insertion subsystem 2406 may include a plurality of redirect pulleys 2412 rotatably mounted within the center housing 1706. The redirect pulleys 2412 may be configured to redirect the drive cables 2410a,b to/from the shaft 1602 and the insertion spool 2408 as the insertion spool 2408 is rotated during operation. In at least one embodiment, some or all of the redirect pulleys 2412 may be arranged at least partially within a side flange 2414 extending laterally outward from the center housing 1706.

Example operation of the insertion subsystem 2406 is now provided. As the insertion spool 2408 is rotated in a first angular direction (e.g., clockwise), the first drive cable 2410a may be drawn from the shaft 1602 and wound about the insertion spool 2408, and the second drive cable 2410b may simultaneously be dispensed from the insertion spool 2408 and fed to the shaft 1602. Paying in the first drive cable 2410a to the insertion spool 2408 while simultaneously paying out the second drive cable 2410b from the insertion spool 2408 may cause the shaft 1602 to move distally relative to the center housing 1706. In contrast, as the insertion spool 2408 is rotated in a second angular direction (e.g., counter-clockwise), the second drive cable 2410b may be drawn from the shaft 1602 and wound about the insertion spool 2408, and the first drive cable 2410a may simultaneously be dispensed from the insertion spool 2408 and fed to the shaft 1602. Paying in the second drive cable 2410b to the insertion spool 2408 while simultaneously paying out the first drive cable 2410a from the insertion spool 2408 may cause the shaft 1602 to move proximally relative to the center housing 1706.

Self-Winding Cable Instrument—Tensioning

Figure 25:
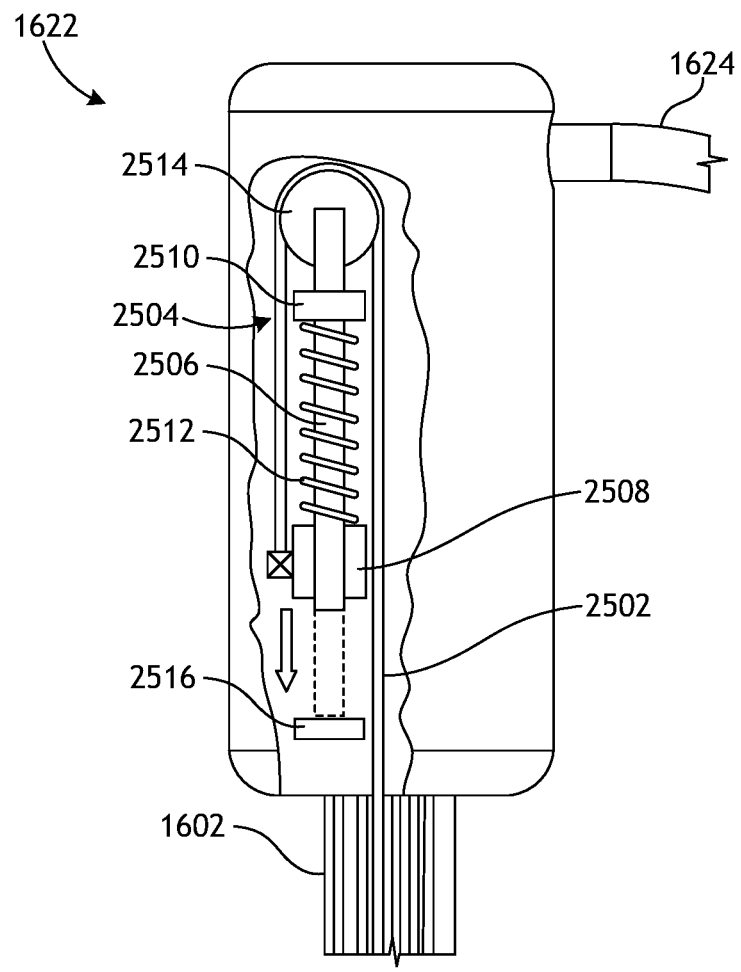
FIG. 25 is an enlarged side view of the tailpiece of FIGS. 16-17, according to one or more embodiments.

FIG. 25 is an enlarged side view of the tailpiece 1622, according to one or more embodiments. As mentioned above, the tailpiece 1622 is arranged at the proximal end of the shaft 1602 and the power cable 1624 extends therefrom to supply electrical power (current) to the surgical tool 1600 (FIGS. 16-17). Some or all of the drive members 1802a-d (FIG. 18) may extend along the shaft 1602 and terminate at the tailpiece 1622. In the illustrated embodiment, a drive member 2502 extends along the shaft 1602 and terminates at the tailpiece 1622. The drive member 2502 may be representative of any of the drive members 1802a-d described herein.

As illustrated, the drive member 2502 may terminate at a cable tensioning assembly 2504 housed within the tailpiece 1622. The cable tensioning assembly 2504 may be configured to maintain tension in the drive member 2502 within the central housing 1706 (FIGS. 17-18) when the surgical tool 1600 (FIGS. 16-17) is detached from the instrument driver 1618 (FIG. 16); e.g., off-robot. While only one cable tensioning assembly 2504 is depicted in FIG. 25, more than one may be included in the tailpiece 1622, without departing from the scope of the disclosure. For instance, the tailpiece 1622 may include separate and discrete cable tensioning assemblies 2504 for each drive member included in the surgical tool 1600 (FIGS. 16-17).

As illustrated, the cable tensioning assembly 2504 may include a tensioning shaft 2506 movably mounted to a stationary portion 2508 of the tailpiece 1622. The tensioning shaft 2506 includes an upper flange 2510, and a compliant member 2512 extends between the stationary portion 2508 and the upper flange 2510. The tensioning shaft 2506 may be configured to extend through or past the stationary portion 2508 during operation, and the compliant member 2512 may be configured to naturally urge the tensioning shaft 2506 away from the stationary portion 2508.

A redirect feature 2514 is mounted to the tensioning shaft 2506, and the drive member 2502 may extend to the cable tensioning assembly 2504 and may be redirected around the redirect feature 2514 to be anchored to the tailpiece 1622. In some embodiments, the redirect feature 2415 comprises a pulley, but in other embodiments the redirect feature may comprise a stationary redirect surface. In at least one embodiment, as illustrated, the drive member 2502 may be anchored to the stationary portion 2508, but may alternatively be anchored to another stationary feature of the tailpiece 1622, without departing from the scope of the disclosure.

Example operation of the cable tensioning assembly 2504 is now provided. As discussed herein, upon mounting the handle 1614 (FIGS. 16, 17, and 20) to the instrument driver 1618 (FIG. 16), the surgical tool 1600 (FIGS. 16-17) may be "homed". This process entails rotating the input stacks 2002 (FIG. 20) to locate and capture a corresponding one of the drive members 1802a-d (FIG. 20) with an associated drive member engagement device 2114 (FIG. 20). With reference to FIG. 25, this "homing" process will engage and pull the drive member 2502 until a predetermined tension is achieved in the drive member 2502. As the drive member 2502 is tensioned, the compliant member 2512 may be compressed between the stationary portion 2508 and the upper flange 2510. In some embodiments, the tensioning shaft 2506 may move until engaging a hard stop 2516 provided within the tailpiece 1622. Once all drive members are properly tensioned with corresponding cable tensioning assemblies 2504, accurate antagonistic cable control may be achieved at the end effector 1604 (FIGS. 16-17) during operation. Upon disengaging the handle 1614 from the instrument driver 1618 (e.g., off-robot), however, the compliant member 2512 may expand to maintain tension in the drive member 2502 within the center housing 1706 (FIGS. 17, 18, and 20).

Alternative embodiments of the cable tensioning assembly 2504 are also contemplated herein. In some embodiments, for example, the redirect feature 2514 may be omitted from the design and the tensioning shaft 2506 may be arranged in line with the drive member 2502; e.g., along the longitudinal axis of the drive member 2502. In such embodiments, the drive member 2502 may alternatively be coupled to an end of tensioning shaft 2502, with the compliant member 2512 extending between the stationary portion 2508 and the upper flange 2510. Moreover, in such embodiments, as the drive member 2502 is tensioned, the compliant member 2512 may be compressed between the stationary portion 2508 and the upper flange 2510 until the tensioning shaft 2506 engages the hard stop 2516. The compliant member 2512 may subsequently expand to maintain tension in the drive member 2502 when the handle 1614 (FIGS. 16, 17, and 20) is disengaged from the instrument driver 1618 (FIG. 16).

Embodiments disclosed herein include:

A. A robotic surgical tool that includes a first assembly including an elongate shaft, a plurality of drive members extending along at least a portion of the shaft, and a center housing movably mounted to the shaft and redirecting the plurality of drive members to and from the shaft, and a second assembly matable with the first assembly to form a handle, the second assembly including a handle housing, a plurality of drive inputs rotatably mounted to the handle housing, and a plurality of input stacks operatively coupled to the plurality of drive inputs such that actuation of the plurality of drive inputs rotates the plurality of input stacks.

B. A robotic surgical tool that includes a handle having a plurality of drive inputs rotatably mounted thereto, an elongate shaft extending through the handle and having an end effector arranged at a distal end thereof, a plurality of drive members extending along the shaft to the end effector, and a plurality of input stacks arranged within the handle and operatively coupled to the plurality of drive inputs such that actuation of the plurality of drive inputs rotates the plurality of input stacks, wherein each input stack includes a drive member engagement device that locates and captures a corresponding one of the plurality of drive members at the handle upon rotation of the input stack.

C. A method of assembling and preparing a robotic surgical tool includes mating a first assembly with a second assembly, the first assembly including an elongate shaft, a plurality of drive members extending along at least a portion of the shaft, and a center housing movably mounted to the shaft and redirecting the plurality of drive members to and from the shaft, and the second assembly including a handle housing, a plurality of drive inputs rotatably mounted to the handle housing, and a plurality of input stacks operatively coupled to the plurality of drive inputs, actuating the plurality of drive inputs and thereby rotating the plurality of input stacks in a first angular direction, and locating and capturing a corresponding one of the plurality of drive members with a drive member engagement device of each input stack upon rotating the plurality of input stacks.

Each of embodiments A, B, and C may have one or more of the following additional elements in any combination: Element 1: wherein each input stack includes a drive member engagement device that locates and captures a corresponding one of the plurality of drive members at the center housing upon rotation of the input stack. Element 2: wherein each input stack further includes a drive shaft extending from a corresponding one of the plurality of drive inputs, first and second spooling pulleys rotatably mounted to the drive shaft, an armature coupled to the drive shaft and interposing the first and second spooling pulleys, the drive member engagement device extending from the armature, and a winding pulley rotatably mounted to the armature and laterally offset from the first and second spooling pulleys, wherein rotating the input stack threads the corresponding one of the plurality of drive members into the winding pulley and the first and second spooling pulleys. Element 3: wherein the center housing provides a plurality of lateral flanges, and a plurality of redirect features provided within the center housing and operable to redirect each drive member to a corresponding one of the plurality of lateral flanges and back to the shaft, wherein the drive member engagement device of each input stack locates and captures the corresponding one of the plurality of drive members at a corresponding one of the plurality of lateral flanges. Element 4: wherein the second assembly further includes a bailout ring extending about the handle housing, and one or more decoupling mechanisms provided on an inner circumferential surface of the bailout ring, wherein manually rotating the bailout ring relative to the handle housing moves the one or more decoupling mechanisms into engagement with the plurality of input stacks and thereby decouples the plurality of input stacks from the plurality of drive inputs, which further allows the drive member engagement device of each input stack to disengage from the corresponding one of the plurality of drive members. Element 5: wherein the one or more decoupling mechanisms comprise at least one of a ramped feature and a ring gear engageable with a pinion gear provided on each input stack. Element 6: wherein each input stack is naturally biased to rotate the drive member engagement device away from a centerline of the center housing. Element 7: further comprising an insertion subsystem arranged within the center housing and including an insertion spool rotatably mounted to an inner cylindrical extension of the center housing, a first drive cable coupled to the insertion spool and anchored to the shaft proximal to the center housing, and a second drive cable coupled to the insertion spool and anchored to the shaft distal to the center housing, wherein rotation of the insertion spool in a first angular direction pays in the first drive cable from the shaft to the insertion spool and simultaneously pays out the second drive cable from the insertion spool to the shaft and thereby moves the shaft distally relative to the center housing, and wherein rotation of the insertion spool in a second angular direction pays in the second drive cable from the shaft to the insertion spool and simultaneously pays out the first drive cable from the insertion spool to the shaft and thereby moves the shaft proximally relative to the center housing. Element 8: wherein the first assembly further includes a tailpiece arranged at a proximal end of the shaft, and a cable tensioning assembly housed within the tailpiece and receiving at least one of the plurality of drive members, the cable tensioning assembly including a tensioning shaft movably mounted to a stationary portion of the tailpiece, a compliant member extending between the stationary portion and an upper flange of the tensioning shaft, and a redirect feature mounted to the tensioning shaft and redirecting the at least one of the plurality of drive members to be anchored to the tailpiece, wherein the cable tensioning assembly maintains tension in the at least one of the plurality of drive members within the central housing when the handle is detached from an instrument driver.

Element 9: wherein the handle is matable with an instrument driver arranged at an end of a robotic arm, the instrument driver providing a plurality of drive outputs matable with the plurality of drive inputs, and wherein the shaft extends through the instrument driver via a central aperture defined longitudinally through the instrument driver. Element 10: wherein each input stack further includes a drive shaft extending from a corresponding one of the plurality of drive inputs, first and second spooling pulleys rotatably mounted to the drive shaft, an armature coupled to the drive shaft and interposing the first and second spooling pulleys, wherein the drive member engagement device extends from the armature, and a winding pulley rotatably mounted to the armature and laterally offset from the first and second spooling pulleys, wherein rotating the input stack threads the corresponding one of the plurality of drive members into the winding pulley and the first and second spooling pulleys. Element 11: wherein the handle provides a center housing that includes a plurality of lateral flanges, and a plurality of redirect features provided within the center housing and operable to redirect each drive member to a corresponding one of the plurality of lateral flanges and back to the shaft, wherein the drive member engagement device of each input stack locates and captures the corresponding one of the plurality of drive members at a corresponding one of the plurality of lateral flanges. Element 12: further comprising an insertion subsystem arranged within the center housing and including an insertion spool rotatably mounted to an inner cylindrical extension of the center housing, a first drive cable coupled to the insertion spool and anchored to the shaft proximal to the handle, a second drive cable coupled to the insertion spool and anchored to the shaft distal to the handle, wherein rotation of the insertion spool in a first angular direction pays in the first drive cable from the shaft to the insertion spool and pays out the second drive cable from the insertion spool to the shaft and thereby moves the shaft distally relative to the handle, and wherein rotation of the insertion spool in a second angular direction pays in the second drive cable from the shaft to the insertion spool and pays out the first drive cable from the insertion spool to the shaft and thereby moves the shaft proximally relative to the handle. Element 13: wherein the handle provides a bailout ring, and one or more decoupling mechanisms provided on an inner circumferential surface of the bailout ring, wherein manually rotating the bailout ring moves the one or more decoupling mechanisms into engagement with the plurality of input stacks and thereby decouples the plurality of input stacks from the plurality of drive inputs and thereby further allows the drive member engagement device of each input stack to disengage from the corresponding one of the plurality of drive members. Element 14: further comprising a tailpiece arranged at a proximal end of the shaft, a cable tensioning assembly housed within the tailpiece and receiving at least one of the plurality of drive members, the cable tensioning assembly including a tensioning shaft movably mounted to a stationary portion of the tailpiece, and a compliant member extending between the stationary portion and an upper flange of the tensioning shaft, wherein the cable tensioning assembly maintains tension in the at least one of the plurality of drive members within the central housing when the handle is detached from an instrument driver.

Element 15: wherein each input stack further includes a drive shaft extending from a corresponding one of the plurality of drive inputs, first and second spooling pulleys rotatably mounted to the drive shaft, an armature coupled to the drive shaft and interposing the first and second spooling pulleys, the drive member engagement device extending from the armature, and a winding pulley rotatably mounted to the armature and laterally offset from the first and second spooling pulleys, the method further comprising rotating each input stack further in the first angular direction and thereby threading the plurality of drive members into the winding pulley and the first and second spooling pulleys of each input stack. Element 16: wherein the center housing provides a plurality of lateral flanges and a plurality of redirect features are provided within the center housing and operable to redirect each drive member to a corresponding one of the plurality of lateral flanges and back to the shaft, the method further comprising locating and capturing the corresponding one of the plurality of drive members at a corresponding one of the plurality of lateral flanges with the armature. Element 17: wherein each lateral flange defines a notch across which a corresponding one of the plurality of drive members extends to be captured by the armature, the method further comprising securing the first assembly to the second assembly by rotating one or more of the input stacks until the armature of the corresponding input stack is received within the notch, and assuming axial surge loads along the shaft at the armature of the corresponding input stack during operation of the robotic surgical tool. Element 18: wherein the second assembly further includes a bailout ring and one or more decoupling mechanisms provided on an inner circumferential surface of the bailout ring, the method further comprising manually rotating the bailout ring relative to the handle housing and thereby moving the one or more decoupling mechanisms into engagement with the plurality of input stacks, decoupling the plurality of input stacks from the plurality of drive inputs as the one or more decoupling mechanisms are moved into engagement with the plurality of input stacks, and rotating each input stack in a second angular direction and thereby disengaging the drive member engagement device of each input stack from the corresponding one of the plurality of drive members. Element 19: wherein the first assembly further includes an insertion subsystem arranged within the center housing and including an insertion spool rotatably mounted to an inner cylindrical extension of the center housing, a first drive cable coupled to the insertion spool and anchored to the shaft proximal to the center housing, and a second drive cable coupled to the insertion spool and anchored to the shaft distal to the center housing, the method further comprising rotating the insertion spool to pay in the first drive cable from the shaft to the insertion spool and pay out the second drive cable from the insertion spool to the shaft and thereby moving the shaft distally relative to the center housing, and rotating the insertion spool to pays in the second drive cable from the shaft to the insertion spool and pay out the first drive cable from the insertion spool to the shaft and thereby moving the shaft proximally relative to the center housing.

By way of non-limiting example, exemplary combinations applicable to A, B, and C include: Element 1 with Element 2; Element 1 with Element 3; Element 1 with Element 4; Element 4 with Element 5; Element 4 with Element 6; Element 11 with Element 12; Element 15 with Element 16; and Element 16 with Element 17.

3. Implementing Systems and Terminology

Implementations disclosed herein provide systems, methods and apparatus for instruments for use with robotic systems. It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

As used herein, the terms "generally" and "substantially" are intended to encompass structural or numeral modification which do not significantly affect the purpose of the element or number modified by such term.

To aid the Patent Office and any readers of this application and any resulting patent in interpreting the claims appended herein, applicants do not intend any of the appended claims or claim elements to invoke 35 U. S. C. 112(f) unless the words "means for" or "step for" are explicitly used in the particular claim.

The foregoing previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotic surgical tool, comprising:
    a first assembly including an elongate shaft, a plurality of drive members extending along at least a portion of the shaft, and a center housing movably mounted to the shaft to allow the center housing to translate along the length of the shaft, the center housing further redirecting the plurality of drive members to and from the shaft; and
    a second assembly matable with the first assembly to form a handle, the second assembly including a handle housing, a plurality of drive inputs rotatably mounted to the handle housing, and a plurality of input stacks operatively coupled to the plurality of drive inputs such that actuation of the plurality of drive inputs rotates the plurality of input stacks;
    wherein the elongate shaft of the first assembly is insertable through the handle housing of the second assembly.

2. The robotic surgical tool of claim 1, wherein each input stack includes a drive member engagement device that locates and captures a corresponding one of the plurality of drive members at the center housing upon rotation of the input stack.

3. The robotic surgical tool of claim 2, wherein each input stack further includes:
    a drive shaft extending from a corresponding one of the plurality of drive inputs;
    first and second spooling pulleys rotatably mounted to the drive shaft;
    an armature coupled to the drive shaft and interposing the first and second spooling pulleys, the drive member engagement device extending from the armature; and
    a winding pulley rotatably mounted to the armature and laterally offset from the first and second spooling pulleys, wherein rotating the input stack threads the corresponding one of the plurality of drive members into the winding pulley and the first and second spooling pulleys.

4. The robotic surgical tool of claim 2, wherein the center housing provides:
    a plurality of lateral flanges; and
    a plurality of redirect features provided within the center housing and operable to redirect each drive member to a corresponding one of the plurality of lateral flanges and back to the shaft,
    wherein the drive member engagement device of each input stack locates and captures the corresponding one of the plurality of drive members at a corresponding one of the plurality of lateral flanges.

5. The robotic surgical tool of claim 2, wherein the second assembly further includes:
    a bailout ring extending about the handle housing; and
    one or more decoupling mechanisms provided on an inner circumferential surface of the bailout ring,
    wherein manually rotating the bailout ring relative to the handle housing moves the one or more decoupling mechanisms into engagement with the plurality of input stacks and thereby decouples the plurality of input stacks from the plurality of drive inputs, which further allows the drive member engagement device of each input stack to disengage from the corresponding one of the plurality of drive members.

6. The robotic surgical tool of claim 5, wherein the one or more decoupling mechanisms comprise at least one of a ramped feature and a ring gear engageable with a pinion gear provided on each input stack.

7. The robotic surgical tool of claim 5, wherein each input stack is naturally biased to rotate the drive member engagement device away from a centerline of the center housing.

8. The robotic surgical tool of claim 1, further comprising an insertion subsystem arranged within the center housing and including:
    an insertion spool rotatably mounted to an inner cylindrical extension of the center housing;
    a first drive cable coupled to the insertion spool and anchored to the shaft proximal to the center housing; and a second drive cable coupled to the insertion spool and anchored to the shaft distal to the center housing, wherein rotation of the insertion spool in a first angular direction pays in the first drive cable from the shaft to the insertion spool and simultaneously pays out the second drive cable from the insertion spool to the shaft and thereby moves the shaft distally relative to the center housing, and wherein rotation of the insertion spool in a second angular direction pays in the second drive cable from the shaft to the insertion spool and simultaneously pays out the first drive cable from the insertion spool to the shaft and thereby moves the shaft proximally relative to the center housing.

9. The robotic surgical tool of claim 1, wherein the first assembly further includes:

a tailpiece arranged at a proximal end of the shaft; and a cable tensioning assembly housed within the tailpiece and receiving at least one of the plurality of drive members, the cable tensioning assembly including:

a tensioning shaft movably mounted to a stationary portion of the tailpiece;

a compliant member extending between the stationary portion and an upper flange of the tensioning shaft; and a redirect feature mounted to the tensioning shaft and redirecting the at least one of the plurality of drive members to be anchored to the tailpiece, wherein the cable tensioning assembly maintains tension in the at least one of the plurality of drive members within the central housing when the handle is detached from an instrument driver.

10. The robotic surgical tool of claim 1, further comprising:

a tailpiece arranged at a proximal end of the shaft;

a cable tensioning assembly housed within the tailpiece and receiving at least one of the plurality of drive members, the cable tensioning assembly including:

a tensioning shaft movably mounted to a stationary portion of the tailpiece; and a compliant member extending between the stationary portion and an upper flange of the tensioning shaft, wherein the cable tensioning assembly maintains tension in the at least one of the plurality of drive members within the central housing when the handle is detached from an instrument driver.

11. A robotic surgical tool, comprising:

a handle having a plurality of drive inputs rotatably mounted thereto;

an elongate shaft extending through the handle and having an end effector arranged at a distal end thereof;

a center housing movably mounted to the shaft and translatable along the length thereof;

a plurality of drive members extending along the shaft to the end effector; and a plurality of input stacks arranged within the handle and operatively coupled to the plurality of drive inputs such that actuation of the plurality of drive inputs rotates the plurality of input stacks, wherein each input stack includes a drive member engagement device that locates and captures a corresponding one of the plurality of drive members at the handle upon rotation of the input stack.

12. The robotic surgical tool of claim 11, wherein the handle is matable with an instrument driver arranged at an end of a robotic arm, the instrument driver providing a plurality of drive outputs matable with the plurality of drive inputs, and wherein the shaft extends through the instrument driver via a central aperture defined longitudinally through the instrument driver.

13. The robotic surgical tool of claim 11, wherein each input stack further includes:

a drive shaft extending from a corresponding one of the plurality of drive inputs;

first and second spooling pulleys rotatably mounted to the drive shaft;

an armature coupled to the drive shaft and interposing the first and second spooling pulleys, wherein the drive member engagement device extends from the armature; and a winding pulley rotatably mounted to the armature and laterally offset from the first and second spooling pulleys, wherein rotating the input stack threads the corresponding one of the plurality of drive members into the winding pulley and the first and second spooling pulleys.

14. The robotic surgical tool of claim 11, wherein the center housing includes:

a plurality of lateral flanges; and a plurality of redirect features provided within the center housing and operable to redirect each drive member to a corresponding one of the plurality of lateral flanges and back to the shaft, wherein the drive member engagement device of each input stack locates and captures the corresponding one of the plurality of drive members at a corresponding one of the plurality of lateral flanges.

15. The robotic surgical tool of claim 14, further comprising an insertion subsystem arranged within the center housing and including:

an insertion spool rotatably mounted to an inner cylindrical extension of the center housing;

a first drive cable coupled to the insertion spool and anchored to the shaft proximal to the handle;

a second drive cable coupled to the insertion spool and anchored to the shaft distal to the handle, wherein rotation of the insertion spool in a first angular direction pays in the first drive cable from the shaft to the insertion spool and pays out the second drive cable from the insertion spool to the shaft and thereby moves the shaft distally relative to the handle, and wherein rotation of the insertion spool in a second angular direction pays in the second drive cable from the shaft to the insertion spool and pays out the first drive cable from the insertion spool to the shaft and thereby moves the shaft proximally relative to the handle.

16. The robotic surgical tool of claim 11, wherein the handle provides:

a bailout ring; and one or more decoupling mechanisms provided on an inner circumferential surface of the bailout ring, wherein manually rotating the bailout ring moves the one or more decoupling mechanisms into engagement with the plurality of input stacks and thereby decouples the plurality of input stacks from the plurality of drive inputs and thereby further allows the drive member engagement device of each input stack to disengage from the corresponding one of the plurality of drive members.

17. A method of assembling and preparing a robotic surgical tool, comprising:
mating a first assembly with a second assembly, the first assembly including an elongate shaft, a plurality of drive members extending along at least a portion of the shaft, and a center housing movably mounted to the shaft to allow the center housing to translate along the length of the shaft, the center housing further redirecting the plurality of drive members to and from the shaft, and the second assembly including a handle housing, a plurality of drive inputs rotatably mounted to the handle housing, and a plurality of input stacks operatively coupled to the plurality of drive inputs, wherein mating the first assembly with the second assembly comprises inserting the elongate shaft of the first assembly through the handle housing of the second assembly;
actuating the plurality of drive inputs and thereby rotating the plurality of input stacks in a first angular direction; and
locating and capturing a corresponding one of the plurality of drive members with a drive member engagement device of each input stack upon rotating the plurality of input stacks.

18. The method of claim 17, wherein each input stack further includes a drive shaft extending from a corresponding one of the plurality of drive inputs, first and second spooling pulleys rotatably mounted to the drive shaft, an armature coupled to the drive shaft and interposing the first and second spooling pulleys, the drive member engagement device extending from the armature, and a winding pulley rotatably mounted to the armature and laterally offset from the first and second spooling pulleys, the method further comprising:
rotating each input stack further in the first angular direction and thereby threading the plurality of drive members into the winding pulley and the first and second spooling pulleys of each input stack.

19. The method of claim 18, wherein the center housing provides a plurality of lateral flanges and a plurality of redirect features are provided within the center housing and operable to redirect each drive member to a corresponding one of the plurality of lateral flanges and back to the shaft, the method further comprising:
locating and capturing the corresponding one of the plurality of drive members at a corresponding one of the plurality of lateral flanges with the armature.

20. The method of claim 19, wherein each lateral flange defines a notch across which a corresponding one of the plurality of drive members extends to be captured by the armature, the method further comprising:
securing the first assembly to the second assembly by rotating one or more of the input stacks until the armature of the corresponding input stack is received within the notch; and
assuming axial surge loads along the shaft at the armature of the corresponding input stack during operation of the robotic surgical tool.

21. The method of claim 17, wherein the second assembly further includes a bailout ring and one or more decoupling mechanisms provided on an inner circumferential surface of the bailout ring, the method further comprising:
manually rotating the bailout ring relative to the handle housing and thereby moving the one or more decoupling mechanisms into engagement with the plurality of input stacks;
decoupling the plurality of input stacks from the plurality of drive inputs as the one or more decoupling mechanisms are moved into engagement with the plurality of input stacks; and
rotating each input stack in a second angular direction and thereby disengaging the drive member engagement device of each input stack from the corresponding one of the plurality of drive members.

22. The method of claim 17, wherein the first assembly further includes an insertion subsystem arranged within the center housing and including an insertion spool rotatably mounted to an inner cylindrical extension of the center housing, a first drive cable coupled to the insertion spool and anchored to the shaft proximal to the center housing, and a second drive cable coupled to the insertion spool and anchored to the shaft distal to the center housing, the method further comprising:
rotating the insertion spool to pay in the first drive cable from the shaft to the insertion spool and pay out the second drive cable from the insertion spool to the shaft and thereby moving the shaft distally relative to the center housing; and
rotating the insertion spool to pays in the second drive cable from the shaft to the insertion spool and pay out the first drive cable from the insertion spool to the shaft and thereby moving the shaft proximally relative to the center housing.

* * * * *